(12) United States Patent
Feltin et al.

(10) Patent No.: US 9,000,051 B2
(45) Date of Patent: Apr. 7, 2015

(54) COSMETIC COMPOSITION BASED ON A SUPRAMOLECULAR POLYMER AND AN ABSORBENT FILLER

(75) Inventors: Charlotte Feltin, Paris (FR); Gaelle Brun, Paris (FR)

(73) Assignee: L'Oreal, Paris (FR)

( * ) Notice: Subject to any disclaimer, the term of this patent is extended or adjusted under 35 U.S.C. 154(b) by 171 days.

(21) Appl. No.: 13/700,056

(22) PCT Filed: May 25, 2011

(86) PCT No.: PCT/IB2011/052280
§ 371 (c)(1),
(2), (4) Date: Jan. 30, 2013

(87) PCT Pub. No.: WO2011/148327
PCT Pub. Date: Dec. 1, 2011

(65) Prior Publication Data
US 2013/0150457 A1    Jun. 13, 2013

Related U.S. Application Data

(60) Provisional application No. 61/344,146, filed on Jun. 1, 2010.

(30) Foreign Application Priority Data

May 26, 2010    (FR) ...................... 10 02233

(51) Int. Cl.
| A01N 37/10 | (2006.01) |
| A61K 31/19 | (2006.01) |
| A01N 37/08 | (2006.01) |
| A61K 8/25 | (2006.01) |
| A61K 8/49 | (2006.01) |
| A61K 8/91 | (2006.01) |
| A61Q 1/02 | (2006.01) |
| A61Q 1/04 | (2006.01) |
| A61K 8/81 | (2006.01) |
| A61Q 1/00 | (2006.01) |

(52) U.S. Cl.
CPC ................ *A61K 8/25* (2013.01); *A61K 8/4953* (2013.01); *A61K 8/91* (2013.01); *A61Q 1/02* (2013.01); *A61Q 1/04* (2013.01); *A61K 8/8111* (2013.01); *A61K 8/8152* (2013.01); *A61Q 1/00* (2013.01)

(58) Field of Classification Search
USPC .................................. 514/770, 772
See application file for complete search history.

(56) References Cited

U.S. PATENT DOCUMENTS

| 2,676,182 | A | 4/1954 | Daudt et al. |
| 3,627,851 | A | 12/1971 | Brady |
| 3,772,247 | A | 11/1973 | Flannigan |
| 4,935,484 | A | 6/1990 | Wolfgruber et al. |
| 5,061,481 | A | 10/1991 | Suzuki et al. |
| 5,082,706 | A | 1/1992 | Tangney |
| 5,219,560 | A | 6/1993 | Suzuki et al. |
| 5,248,739 | A | 9/1993 | Schmidt et al. |
| 5,302,685 | A | 4/1994 | Tsumura et al. |
| 5,319,040 | A | 6/1994 | Wengrovius et al. |
| 5,817,302 | A | 10/1998 | Berthiaume et al. |
| 5,874,069 | A | 2/1999 | Mendolia et al. |
| 5,919,441 | A | 7/1999 | Mendolia et al. |
| 5,981,680 | A | 11/1999 | Petroff et al. |
| 6,051,216 | A | 4/2000 | Barr et al. |
| 8,709,388 | B2 | 4/2014 | Tong et al. |
| 8,846,015 | B2 | 9/2014 | Tong et al. |
| 2004/0161394 | A1 * | 8/2004 | Mougin et al. ............. 424/70.11 |
| 2008/0003195 | A1 | 1/2008 | Arnaud et al. |
| 2008/0281008 | A1 | 11/2008 | Styczen et al. |
| 2010/0158832 | A1 | 6/2010 | Chodorowski-Kimmes et al. |
| 2013/0136705 | A1 | 5/2013 | Chodorowski-Kimmes et al. |
| 2013/0142743 | A1 | 6/2013 | Cavazzuti et al. |
| 2013/0150457 | A1 | 6/2013 | Feltin et al. |
| 2013/0195778 | A1 | 8/2013 | Chodorowski-Kimmes et al. |
| 2013/0236408 | A1 | 9/2013 | Bui et al. |
| 2013/0236409 | A1 | 9/2013 | Bui et al. |

FOREIGN PATENT DOCUMENTS

| CN | 101084863 A | 12/2007 |
| CN | 101301254 A | 11/2008 |
| EP | 0 748 746 A1 | 12/1996 |
| EP | 0 749 747 A1 | 12/1996 |
| EP | 0 923 928 A1 | 6/1999 |
| EP | 0 930 060 A1 | 7/1999 |
| EP | 0 963 751 A2 | 12/1999 |
| EP | 2 189 148 A2 | 5/2010 |
| EP | 2 189 151 A1 | 5/2010 |
| FR | 2 782 723 A1 | 3/2000 |
| FR | 2 825 628 A1 | 12/2002 |
| FR | 2 938 758 A1 | 5/2010 |

(Continued)

OTHER PUBLICATIONS

Jul. 25, 2011 Written Opinion issued in International Patent Application No. PCT/IB2011/052280.

Mar. 8, 2011 Preliminary Search Report issued in French Patent Application No. FR1002233.

Mar. 8, 2011 Written Opinion issued in French Patent Application No. FR1002233 (w/translation).

Jan. 26, 2012 Search Report issued in International Patent Application No. PCT/IB2011/052281.

(Continued)

*Primary Examiner* — Trevor Love
(74) *Attorney, Agent, or Firm* — Oliff PLC

(57) ABSTRACT

The present invention relates mainly to a cosmetic composition and in particular a composition for making up and/or caring for keratin material and more particularly the skin and/or the lips, including at least one supramolecular polymer and a filler with an oil uptake of greater than or equal to 1.5 ml/g.

11 Claims, No Drawings

(56) References Cited

FOREIGN PATENT DOCUMENTS

| | | |
|---|---|---|
| FR | 2 946 872 A1 | 12/2010 |
| JP | A-9-171154 | 6/1997 |
| WO | WO 03/032929 A2 | 4/2003 |
| WO | WO 03/045337 A2 | 6/2003 |
| WO | WO 2004/055081 A2 | 7/2004 |
| WO | WO 2005/042641 A1 | 5/2005 |
| WO | WO 2005/075542 A1 | 8/2005 |
| WO | WO 2009/101320 A2 | 8/2009 |
| WO | WO 2010/057920 A2 | 5/2010 |
| WO | WO 2010/146147 A2 | 12/2010 |
| WO | 2011/147696 A1 | 12/2011 |
| WO | 2011/147697 A1 | 12/2011 |
| WO | 2011/148327 A1 | 12/2011 |
| WO | 2011/148328 A2 | 12/2011 |

OTHER PUBLICATIONS

U.S. Appl. No. 13/700,029, in the name of Cavazzuti et al., filed Jan. 30, 2013.

U.S. Appl. No. 13/691,134, in the name of Cavazzuti et al., filed Nov. 30, 2012.

Office Action issued in Chinese Patent Application No. 201180037044.6 dated Dec. 13, 2013 (with partial translation).

Oct. 10, 2014 Office Action issued in Chinese Application No. 201180036985.8 (with English translation).

Nov. 3, 2014 Office Action issued in U.S. Appl. No. 13/700,029.

Jan. 27, 2015 Office Action issued in U.S. Appl. No. 13/691,134.

\* cited by examiner

COSMETIC COMPOSITION BASED ON A SUPRAMOLECULAR POLYMER AND AN ABSORBENT FILLER

The present invention relates mainly to a cosmetic composition and in particular a composition for making up and/or caring for keratin material and more particularly the skin and/or the lips, comprising at least one supramolecular polymer and a filler with an oil uptake of greater than or equal to 1.5 ml/g.

In general, when women use a makeup product, especially of foundation type, they wish this product to have, after application, good remanence on the skin, and in particular for it not to transfer onto clothing.

With regard to this expectation, one or more polymers that are specifically dedicated towards affording these improved remanence properties over time are commonly introduced into compositions of this type. Illustrations of these polymers that may particularly be mentioned include silicone resins, polyacrylates and latices.

However, the abovementioned polymers that are advantageous in terms of remanence properties, and in particular of transfer resistance properties, are unfortunately liable to give rise to a sensation of discomfort during application (difficult, tacky spreading) and/or after application (tautness, mask effect) of the cosmetic product containing them.

Supramolecular polymers such as those described in patent applications EP 2 189 151 and FR 2 938 758 are, on the other hand, known to allow the production on the skin of a deposit that is both comfortable and endowed with improved remanence properties over time, in particular remanence of the colour of the deposit (no embrittlement or fragmentation of the deposit, which remains uniform). However, the user has a sensation of "tackiness" during the application and drying on the skin of products incorporating these supramolecular polymers.

The inventors have found, unexpectedly, that it turns out to be possible to overcome this drawback provided that such supramolecular polymers are used in combination with a filler with an oil uptake of greater than or equal to 1.5 ml/g. This combination makes it possible especially to reduce the tack of the said composition after application thereof to keratin materials; the deposit is thus more comfortable and less tacky immediately after application.

The aim of the present invention is thus to overcome the abovementioned drawbacks and to propose a cosmetic composition that is capable, on the one hand, of affording good cosmetic properties such as good adhesion to the support (skin) and thus good remanence of the composition, where appropriate good sheen, and, on the other hand, of forming a non-tacky or sparingly tacky deposit that is particularly resistant to external attack by fatty substances (oil, meals or sebum) and also to friction, resulting in less wear of the deposit.

Thus, according to one of its aspects, the present invention relates to a cosmetic process for making up and/or caring for the skin and/or the lips, comprising, in a physiologically acceptable medium, at least one supramolecular polymer based on a functionalized polyalkene of formula HO—P—OH in which P represents a homopolymer or a copolymer that may be obtained by polymerization of one or more linear, cyclic and/or branched or polyunsaturated $C_2$-$C_{10}$ and preferably $C_2$-$C_4$ alkenes, which may be derived from the reaction, especially the condensation, of the said functionalized polyalkene polymer with at least one junction group functionalized with at least one reactive group capable of reacting with the reactive group(s) of the functionalized polyalkene polymer, the said junction group being capable of forming at least 3 H (hydrogen) bonds, preferably at least 4 H bonds, preferentially 4 H bonds, and at least one filler with an oil uptake, measured according to the method of measuring the wet point as described in the specification, of greater than or equal to 1.5 ml/g.

For the purposes of the present invention, the term "physiologically acceptable medium" is intended to denote a medium that is suitable for the application of a composition to the skin and/or the lips, in particular the skin and especially of the face.

As emerges from the examples below, the combination under consideration according to the invention proves to be most particularly effective for affording a composition that simultaneously has improved remanence over time, in particular of remanence of the colour of the deposit (no embrittlement or fragmentation of the deposit, which remains homogeneous) and satisfactory comfort properties, both on application and during wearing (no tacky sensation, or sensation of tautness or dryness especially).

This particular embodiment may thus especially allow the production of compositions, especially makeup compositions, whose deposition on keratin materials, and in particular the lips and/or the skin, is uniform and/or sparingly tacky or non-tacky. Such a deposit may especially afford a sensation of comfort to the wearer (softness, glidance of the deposit formed).

In addition, such a composition may have improved properties in terms of transfer resistance, remanence of the deposit, especially in terms of colour (no embrittlement or fragmentation of the deposit, which remains uniform and/or resistant to friction), and of resistance to fats.

According to another of its aspects, the present invention relates to a cosmetic process for making up and/or caring for the skin and/or the lips, comprising at least the application to the said skin and/or the said lips of a composition according to the invention.

The compositions under consideration according to the invention may be in solid or liquid form at 20° C.

It may especially be, in particular in the case of a composition of foundation type, a loose or compact powder or a liquid formulation that may be anhydrous or of the oil-in-water or water-in-oil emulsion type.

Advantageously, the compositions according to the invention are anhydrous.

According to one particular embodiment, the composition is used for application to the skin, advantageously to greasy skin.

For the purposes of the invention, the term "solid" characterizes the state of the composition at a temperature of 20° C. In particular, a solid composition according to the invention has, at a temperature of 20° C. and at atmospheric pressure (760 mmHg), a hardness of greater than 30 $Nm^{-1}$ and preferably greater than 40 $Nm^{-1}$.

Protocol for Measuring the Hardness:

The hardness of the composition is measured according to the following protocol:

The stick of lipstick is stored at 20° C. for 24 hours before measuring the hardness.

The hardness may be measured at 20° C. via the "cheese wire" method, which consists in transversely cutting a wand of product, which is preferably a circular cylinder, by means of a rigid tungsten wire 250 µm in diameter, by moving the wire relative to the stick at a speed of 100 mm/minute.

The hardness of the samples of compositions of the invention, expressed in $Nm^{-1}$, is measured using a DFGS2 tensile testing machine from the company Indelco-Chatillon.

The measurement is repeated three times and then averaged. The average of the three values read using the tensile testing machine mentioned above, noted Y, is given in grains. This average is converted into newtons and then divided by L which represents the longest distance through which the wire passes. In the case of a cylindrical wand, L is equal to the diameter (in metres).

The hardness is converted into $Nm^1$ by the equation below:

$$Y \times 10^{-3} \times 9.8)/L$$

For a measurement at a different temperature, the stick is stored for 24 hours at this new temperature before the measurement.

According to this measuring method, a solid composition according to the invention has a hardness at 20° C. of greater than or equal to 30 $Nm^{-1}$, preferably greater than 40 $Nm^{-1}$ and preferably greater than 50 $Nm^{-1}$.

Preferably, the composition according to the invention especially has a hardness at 20° C. of less than 500 $Nm^{-1}$ especially less than 400 $Nm^{-1}$ and preferably less than 300 $Nm^{-1}$.

In particular, a composition whose hardness is greater than 30 $Nm^{-1}$ is said to be "solid" at 20° C. and at atmospheric pressure (760 mmHg).

A composition according to the invention may be in the form of a skin and/or lip makeup composition, especially for facial or bodily skin; it may be a complexion product such as a foundation, a face powder or an eyeshadow; a lip product such as a lipstick or a lipcare product; a concealer product; a blusher; an eyeliner; a lip pencil or an eye pencil; a body makeup product; a gloss (lip gloss).

According to a first advantageous embodiment of the invention, the composition according to the invention is intended for making up the skin and it is then more particularly a foundation, a face powder, an eyeshadow or a body makeup product.

According to a second advantageous embodiment of the invention, the composition according to the invention is intended for making up the lips and it is then more particularly a lipstick (lipstick wand) or a gloss (liquid lipstick).

Supramolecular Polymer

The cosmetic compositions according to the invention thus comprise a polyalkene-based (i.e. polyolefin) supramolecular polymer.

For the purposes of the present invention, the term "polyalkene-based supramolecular polymer" means a polymer derived from the reaction, especially the condensation, of at least one polyalkene polymer functionalized with at least one reactive group, with at least one junction group functionalized with at least one reactive group capable of reacting with the reactive group(s) of the functionalized polyalkene polymer, said junction group being capable of forming at least three H (hydrogen) bonds and preferably at least four H bonds, preferentially four H bonds.

The term "polyalkene" or "polyolefin" means a polymer derived from the polymerization of at least one monomer of alkene type, comprising an ethylenic unsaturation, the said monomer possibly being pendent or in the main chain of the said polymer. The term "polyalkene" or "polyolefin" is thus directed towards polymers that may or may not comprise a double bond. Preferably, the supramolecular polymers used according to the invention are prepared from a polymer derived from the polymerization of an alkene comprising at least two ethylenic unsaturations.

The supramolecular polymer according to the invention is capable of forming a supramolecular polymer chain or network, by (self)assembly of said polymer according to the invention with at least one other identical or different polymer according to the invention, each assembly involving at least one pair of paired junction groups, which may be identical or different, borne by each of the polymers according to the invention.

For the purposes of the invention, the term "junction group" means any group comprising groups that donate or accept H bonds, and capable of forming at least three H bonds and preferably at least four H bonds, preferentially four H bonds, with an identical or different partner junction group. These junction groups may be lateral to the polymer backbone (side branching) and/or borne by the ends of the polymer backbone, and/or in the chain forming the polymer backbone. They may be distributed in a random or controlled manner.

Functionalized Polyalkene

The polyalkene polymers are functionalized with at least one reactive group and preferably with at least two reactive groups. The functionalization preferably Occurs at the chain ends. They are then referred to as telechelic polymers.

The functionalization groups, or reactive groups, may be attached to the polyalkene polymer via linkers, preferably linear or branched $C_1$-$C_4$ alkylene groups, or directly via a single bond.

Preferably, the functionalized polyalkene polymers have a number-average molecular mass (Mn) of between 1000 and 8000.

Even more preferably, they have a number-average molecular mass of between 1000 and 5000, or even between 1500 and 4500.

Even more preferably, they have a number-average molecular mass of between 2000 and 4000.

Preferably, the functionalized polyalkene polymer, capable of forming all or part of the polymer backbone of the supramolecular polymer according to the invention (preferably, it forms all of the backbone of the polymer), is of formula HO—P—OH in which:

P represents a homo- or copolymer that may be obtained by polymerization of one or more linear, cyclic and/or branched, polyunsaturated (preferably diunsaturated) $C_2$-$C_{10}$ and preferably $C_2$-$C_4$ alkenes.

P preferably represents a homo- or copolymer that may be obtained by polymerization of one or more linear or branched, $C_2$-$C_4$ diunsaturated alkenes.

More preferably, P represents a polymer chosen from a polybutylene, a polybutadiene (such as a 1,4-polybutadiene or a 1,2-polybutadiene), a polyisoprene, a poly(1,3-pentadiene) and a polyisobutylene, and copolymers thereof.

According to one preferred embodiment, P represents a poly(ethylene/butylene) copolymer.

The preferred poly(ethylene/butylenes) are copolymers of 1-butene and of ethylene. They may be represented schematically by the following sequence of units:

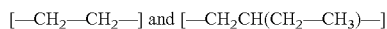

[—$CH_2$—$CH_2$—] and [—$CH_2CH(CH_2$—$CH_3$)—]

According to a second preferred embodiment, P is a polybutadiene homopolymer, preferably chosen from a 1,4-polybutadiene or a 1,2-polybutadiene. The polybutadienes may be 1,4-polybutadienes or 1,2-polybutadienes, which may be represented schematically, respectively, by the following sequences of units:

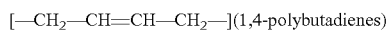

[—$CH_2$—CH=CH—$CH_2$—](1,4-polybutadienes)

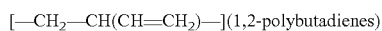

[—$CH_2$—CH(CH=$CH_2$)—](1,2-polybutadienes)

Preferably, they are 1,2-polybutadienes. Preferably, P is a 1,2-polybutadiene homopolymer.

According to another embodiment, P is a polyisoprene. Polyisoprenes may be represented schematically by the following sequences of units:

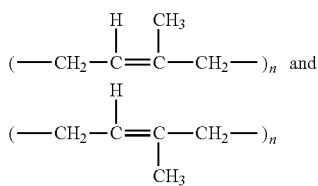

A mixture of above units may obviously also be used, so as to form copolymers.

The functionalized polyalkene polymers may be totally hydrogenated to avoid the risks of crosslinking. Preferably, the functionalized polyalkene polymers used in the compositions according to the invention are hydrogenated.

Preferably, the polyalkene polymers are hydrogenated and functionalized with at least two OH reactive groups, preferably at the ends of the polymers.

Preferably, they have functionality as hydroxyl end groups of from 1.8 to 3 and preferably in the region of 2.

The polydienes containing hydroxyl end groups are especially defined, for example, in FR 2 782 723. They may be chosen from polybutadiene, polyisoprene and poly(1,3-pentadiene) homopolymers and copolymers. Mention will be made in particular of the hydroxylated polybutadienes sold by the company Sartomer, for instance the Krasol® Resins and the Poly Bd® Resins. Preferably, they are dihydroxylated hydrogenated 1,2-polybutadiene homopolymers, such as the range Nisso-PB 1, GI3000, GI2000 and GI1000 sold by the company Nisso, which may be represented schematically by the following formula:

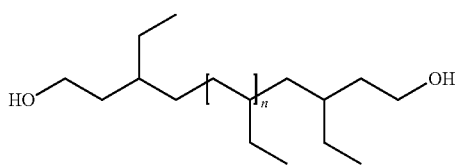

Preferably, n' is between 14 and 105 and preferably between 20 and 85.

These polymers have the following number-average molecular masses: GI3000 of Mn=4700, GI2000 of Mn=3300 and GI1000 of Mn=1500. These values were measured by GPC according to the following protocol:

Protocol for Determining the Molecular Masses of the Supramolecular Polymer by GPC Determination of the number-average molecular mass $\overline{Mn}$, the weight-average molecular mass $\overline{Mw}$ and the polydispersity index $\overline{Mw}/\overline{Mn}$ in polystyrene equivalents.

Preparation of the Standard Solutions

Prepare the polystyrene standards from Varian kits (ref.: PS-H (PL2010-0200)

The masses of the standards are as follows:
PS 6035000-PS 3053000-PS 915000-PS 483000-PS 184900-PS 60450-PS 19720-PS 8450-PS 3370-PS 1260-PS 580

Inject 100 μl of each of the solutions into the calibration column.

Preparation of the Sample:
Prepare a solution with a solids content of 0.5% in THF.
Prepare the solution about 24 hours before injection.
Filter the solution through a Millex FH filter (0.45 μm).
Inject into the column.
Chromatographic Conditions:
Columns: PL Rapid M (batch 5M-Poly-008-15) from Polymer Labs
PL-gel HTS-D (batch 5M-MD-72-2) from Polymer Labs
PL-gel HTS-F (10M-2-169B-25) from Polymer Labs
PL-Rapid-F (6M-0L1-011-6) from Polymer Labs
Length: 150 mm—inside diameter: 7.5 mm
Pump: isocratic M1515 Waters
Eluent: THF
flow rate: 1 ml/minute
Temperature: ambient
Injection: 100 μl at 0.5% AM in the eluent
Detection: RI 64 mV (Waters 2424 refractometer) Temperature: 45° C.
UV at 254 nm at 0.1 OD (Waters 2487 UV detector)
Integrator: Empower option GPC
Determination of the Molar Masses The average molar masses are determined by plotting the calibration curve: log Molar mass=f (elution volume at the top of the RI detection peak) and using the software Empower option GPC from Waters.

Among the polyolefins with hydroxyl end groups, mention may be made preferentially of polyolefins, homopolymers or copolymers with α,ω-hydroxyl end groups, such as polyisobutylenes with α,ω-hydroxyl end groups; and the copolymers of formula:

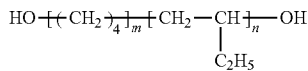

especially those sold by Mitsubishi under the brand name Polytail.

Junction Group

The supramolecular polymers according to the invention also have in their structure at least one residue of a junction group capable of forming at least three H bonds and preferably at least four H bonds, said junction group being initially functionalized with at least one reactive group.

Unless otherwise mentioned, the term "junction group" means in the present description the group without its reactive function.

The reactive groups are attached to the junction group via linkers L.

L is a single bond or a saturated or unsaturated $C_{1-20}$ divalent carbon-based group chosen in particular from a linear or branched $C_1$-$C_{20}$ alkylene; a $C_5$-$C_{20}$ (alkyl)cycloalkylene alkylene (preferably cyclohexylene methylene), a $C_{11}$-$C_{20}$ alkylene-biscycloalkylene (preferably alkylene-biscyclohexylene), a $C_6$-$C_{20}$ (alkyl)arylene, an alkylene-bisarylene (preferably an alkylene-biphenylene), the linker L possibly being substituted with at least one alkyl group and/or possibly comprising 1 to 4 N and/or O heteroatoms, especially in the form of an $NO_2$ substituent.

Preferably, the linker is a group chosen from phenylene; 1,4-nitrophenylene: 1,2-ethylene; 1,6-hexylene; 1,4-butylene; 1,6-(2,4,4-trimethylhexylene); 1,4-(4-methylpentylene): 1,5-(5-methylhexylene): 1,6-(6-methylheptyl ene); 1,5-(2,2,5-trimethylhexylene); 1,7-(3,7-dimethyloctylene); -isophorone-; 4,4'-methylene bis(cyclohexylene); tolylene; 2-methyl-1,3-phenylene; 4-methyl-1,3-phenylene: 4,4-biphenylenemethylene;

Preferably, the linker is chosen from the groups:
$C_5$-$C_{20}$ (alkyl)cycloalkylene alkylene, such as isophorone,
$C_{11}$-$C_{25}$ alkylene-biscycloalkylene, such as 4,4'-methylene biscyclohexylene,
$C_1$-$C_{20}$ alkylene, such as —$(CH_2)_2$—; —$(CH_2)_6$—; —$CH_2CH(CH_3)$—$CH_2$—$C(CH_3)_2$—$CH_2$—$CH_2$, and
$C_6$-$C_{20}$ (alkyl)phenylene, such as 2-methyl-1,3-phenylene.

Preferably, L is chosen from: -isophorone-; —$(CH_2)_2$—; —$(CH_2)_6$—; —$CH_2CH(CH_3)$—$CH_2$—$C(CH_3)_2$—$CH_2$—$CH_2$; 4,4'-methylene bis(cyclohexylene); 2-methyl-1,3-phenylene.

According to one particularly preferred embodiment, the linker is an alkylcycloalkylene alkylene.

Preferably, according to this embodiment, the linker is an isophorone group. The term "isophorone" means the following group:

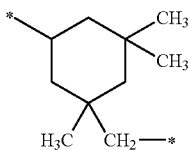

The said reactive groups functionalizing the junction group must be capable of reacting with the —OH reactive group(s) borne by the functionalized polyalkene.

Reactive groups that may be mentioned include isocyanate (—N═C═O) and thioisocyanate (—N═C═S) groups. Preferably, it is a group —N═C═O (isocyanate).

The functionalized junction groups capable of forming at least three H bonds may comprise at least three identical or different functional groups, and preferably at least four functional groups, chosen from:

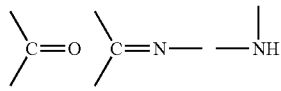

These functional groups may be classified into two categories:

functional groups that donate H bonds:

functional groups that accept H bonds:

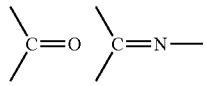

The junction groups capable of forming at least three H bonds form a basic structural element comprising at least three groups, preferably at least four groups and more preferentially four functional groups capable of establishing H bonds. The said basic structural elements capable of establishing H bonds may be represented schematically in the following manner:

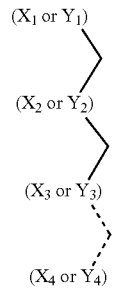

in which $X_i$, is an H-bond accepting functional group (identical or different) and $Y_i$ is an H-bond donating functional group (identical or different).

Thus, each structural element should be able to establish H bonds with one or more partner structural elements, which are identical (i.e. self-complementary) or different, such that each pairing of two partner structural elements takes place by formation of at least three H bonds, preferably at least four H bonds and more preferentially four H bonds.

A proton acceptor X will pair with a proton donor Y. Several possibilities are thus offered, for example pairing of:
XXXX with YYYY;
XXXY with YYYX;
XXYX with YYXY;
XYYX with YXXY;
XXYY with YYXX self-complementary or otherwise;
XYXY with YXYX self-complementary or otherwise.

Preferably, the junction groups may establish four H bonds with an identical (or self-complementary) partner group among which are two donor bonds (for example NH) and two acceptor bonds (for example CO and —C═N—).

Preferably, the junction groups capable of forming at least four H bonds are chosen from the ureidopyrimidones of formula:

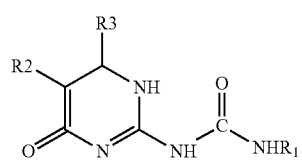

it being understood that all the tautomeric forms are included.

In this formula, the radicals have the following meanings:
the radicals $R_1$ (or the radicals $R_1$ and $R_2$) are single bonds constituting the point of attachment of the junction group to the linker capable of forming at least three H bonds (preferably four H bonds) on the rest of the graft. Preferably, the said point of attachment is borne solely by $R_1$, which is a single bond.

the radical $R_2$ represents a divalent group chosen from a single bond or a $C_1$-$C_6$ alkylene or a monovalent group chosen from a single bond, a hydrogen atom or a linear or branched $C_1$-$C_{10}$ saturated monovalent hydrocarbon-based group, which may contain one or more heteroatoms such as O, S or N, these groups being optionally substituted with a hydroxyl, amino and/or thio function.

Preferably, the radical $R_2$ may be a single bond or a monovalent group chosen from H, $CH_2OH$ and $(CH_2)_2$—OH, $CH_3$.

According to one particularly preferred embodiment, $R_2$ is H.

the radical $R_3$ represents a monovalent or divalent group, in particular, $R_3$ is chosen from a hydrogen atom or a linear or branched $C_1$-$C_{10}$ saturated monovalent hydrocarbon-based group, which may contain one or more heteroatoms such as O, S or N, these groups being optionally substituted with a hydroxyl, amino and/or thio function.

Preferably, the radical $R_3$ may be a monovalent group chosen from H, $CH_2OH$ and $(CH_2)_2$—OH, $CH_3$.

According to one particularly preferred embodiment, $R_3$ is a methyl group.

According to one preferred embodiment, the junction groups are chosen from 2-ureidopyrimidone and 6-methyl-2-ureidopyrimidone.

Preferably, the preferred junction group is 6-methyl-2-ureidopyrimidone.

The junction groups, and especially the ureidopyrimidone junction groups, may be added directly or may be formed in situ during the process for preparing the supramolecular polymer. The first and second preparation methods described below illustrate these two alternatives, respectively.

In particular, the functionalized junction groups capable of reacting with the functionalized polyalkene polymer to give the supramolecular polymer according to the invention are preferably of formula:

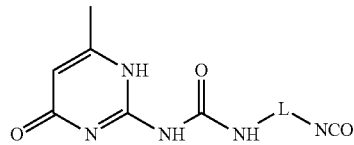

in which L is as defined above.
Preferably, L is chosen from the groups:
$C_5$-$C_{20}$ (alkyl)cycloalkylene alkylene, such as isophorone,
$C_{11}$-$C_{25}$ alkylene-biscycloalkylene, such as 4,4'-methylene biscyclohexylene,
$C_1$-$C_{20}$ alkylene, such as —$(CH_2)_2$—; —$(CH_2)_6$—; —$CH_2CH(CH_3)$—$CH_2$—$C(CH_3)_2$—$CH_2$—$CH_2$—, and
$C_6$-$C_{20}$ (alkyl)phenylene, such as 2-methyl-1,3-phenylene.
Preferably, L is chosen from: -isophorone-; —$(CH_2)_6$—; 4,4'-methylene biscyclohexylene.

According to one particularly preferred embodiment, the junction group is of formula

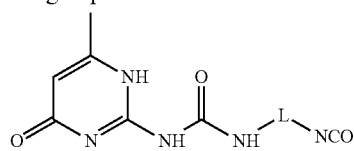

in which L is isophorone.
In one particularly preferred embodiment, the supramolecular polymer of the invention corresponds to the formula:

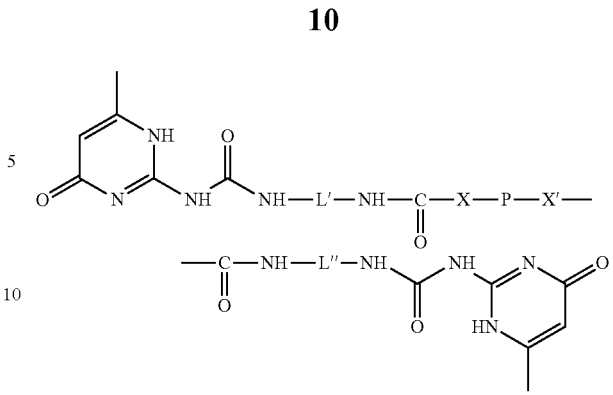

in which:
L' and L" have, independently of each other, the meaning given above for L;
X, X'=O and P has the meaning given above for the functionalized polyalkene polymer.

Preferably, L' and L" represent a saturated or unsaturated $C_1$-$C_{20}$ divalent carbon-based group, chosen in particular from a linear or branched $C_1$-$C_{20}$ alkylene; a $C_5$-$C_{20}$ (alkyl)cycloalkylene, an alkylene-biscycloalkylene and a $C_6$-$C_{20}$ (alkyl)arylene. Preferably, L' and L" represent an isophorone-; —$(CH_2)_2$—; —$(CH_2)_6$—; $CH_2CH(CH_3)$—$CH_2$—$C(CH_3)_2$—$CH_2$—$CH_2$; 4,4'-methylene biscyclohexylene; 2-methyl-1,3-phenylene group.

Preferably, L' and L" are identical.
Preferably, L' and L" are an isophorone group.
Preferably, P is hydrogenated and represents a polyethylene, a polybutylene, a polybutadiene, a polyisoprene, a poly(1,3-pentadiene), a polyisobutylene, or a copolymer thereof, especially a poly(ethylene/butylene).

Preferably, P is a hydrogenated polybutadiene, preferably a hydrogenated 1,2-polybutadiene.

In one particularly preferred embodiment, the supramolecular polymer of the invention corresponds to the formula:

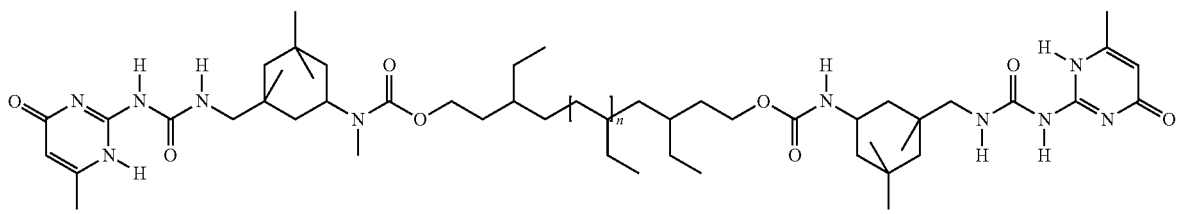

Preparation Process

The polymer according to the invention may be prepared via the processes usually used by a person skilled in the art, especially for forming a urethane bond between the free OH functions of a polyalkene, and the isocyanate functions borne by the junction group.

By way of non-limiting illustration, a first general preparation process consists in:
optionally ensuring that the polymer to be functionalized does not comprise any residual water,
heating the said polymer comprising at least two OH reactive functions to a temperature that may be between 60°

C. and 140° C.; the hydroxyl number of the polymer being able to serve as reference in order to measure the degree of progress of the reaction;

adding, preferably directly, the ureidopyrimidone junction group bearing the reactive functions, especially isocyanate such as those described in patent WO 2005/042 641; especially such as the compounds of CAS numbers 32093-85-9 and 709028-42-2;

optionally stirring the mixture, under a controlled atmosphere, at a temperature of about 90-130° C.; for 1 to 24 hours;

optionally monitoring by infrared spectroscopy the disappearance of the characteristic isocyanate band (between 2500 and 2800 cm$^{-1}$) so as to stop the reaction on total disappearance of the peak, and then allowing the final product to cool to room temperature.

The reaction may also be monitored by assaying the hydroxyl functions: it is also possible to add ethanol in order to ensure the total disappearance of the residual isocyanate functions.

The reaction may be performed in the presence of a solvent, especially methyltetrahydrofuran, tetrahydrofuran, toluene, propylene carbonate or butyl acetate. It is also possible to add a conventional catalyst for forming a urethane bond. An example that may be mentioned is dibutyltin dilaurate. The polymer may finally be washed and dried, or even purified, according to the general knowledge of a person skilled in the art.

According to the second preferred mode of preparation, the reaction may comprise the following steps:

(i) functionalization of the polymer, which has preferably been dried beforehand, with a diisocyanate according to the reaction scheme:

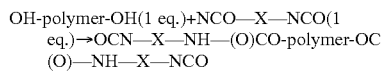

OH-polymer-OH(1 eq.)+NCO—X—NCO(1 eq.)→OCN—X—NH—(O)CO-polymer-OC(O)—NH—X—NCO

The diisocyanate may optionally be in excess relative to the polymer. This first step may be performed in the presence of solvent, at a temperature of between 20° C. and 100° C. This first step may be followed by a period of stirring under a controlled atmosphere for 1 to 24 hours. The mixture may optionally be heated. The degree of progress of this first step may be monitored by assaying the hydroxyl functions.

and then (ii) reaction of the prepolymer obtained above with 6-methylisocytosine of formula:

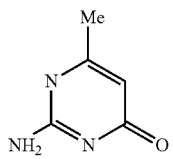

this second step may optionally be performed in the presence of a cosolvent such as toluene, butyl acetate or propylene carbonate. The reaction mixture may be heated to between 80° C. and 140° C. for a time ranging between 1 and 24 hours. The presence of a catalyst, especially dibutyltin dilaurate, may promote the production of the desired final product.

The reaction may be monitored by infrared spectroscopy, by monitoring the disappearance of the characteristic peak of isocyanate between 2200 and 2300 cm$^{-1}$. At the end of the reaction, ethanol may be added to the reaction medium in order to neutralize any residual isocyanate functions. The reaction mixture may be optionally filtered. The polymer may also be stripped directly in a cosmetic solvent.

According to one particular mode, the said supramolecular polymer is dissolved in a hydrocarbon-based oil, which is preferably volatile, in particular isododecane.

Thus, the composition of the invention will comprise at least one hydrocarbon-based oil, which is preferably volatile, in particular at least isododecane, especially provided by the supramolecular polymer solution.

In embodiment variants of a composition and of a process according to the invention, the supramolecular polymer(s) may be present in a composition according to the invention in an amount ranging from 0.1% to 60% by weight of solids, relative to the total weight of the composition.

Thus, the supramolecular polymer(s) may be present in a composition according to the invention in an amount ranging from 0.2% to 50% by weight, relative to the total weight of the composition.

Similarly, the supramolecular polymer(s) may be present in a composition according to the invention in an amount ranging from 0.3% to 40% by weight, relative to the total weight of the composition.

The supramolecular polymer(s) may also be present in a composition according to the invention in an amount ranging from 0.5% to 30% by weight, relative to the total weight of the composition.

Advantageously, a composition according to the invention, in particular in the case of a composition for making up the skin and/or the lips, comprises a content of supramolecular polymer of between 5% and 99% by weight relative to the weight of the composition excluding volatile compound(s) (in particular relative to the weight of the composition excluding volatile oil(s), for instance isododecane).

This content reflects the resulting content of supramolecular polymer(s) in a deposit made with a composition or according to the process of the invention, especially on keratin materials such as the skin and/or the lips, for example, after evaporation of the volatile compounds.

Preferably, the composition according to the invention, in particular in the case of a makeup composition, comprises a content of supramolecular polymer of between 10% and 90% by weight relative to the weight of the composition excluding volatile compound(s), preferably between 15% and 80%.

According to one particular mode, these contents are used for a composition in the form of a composition for caring for and/or making up the skin, especially of the face, in particular a foundation.

In one particular embodiment of the invention, a composition is in the form of a composition for caring for and/or making up the skin, especially of the face (e.g.: a foundation) and the supramolecular polymer(s) may be present therein in a content ranging from 2.5% to 60% by weight of solids relative to the total weight of the composition.

In another embodiment, a composition is in the form of a composition for caring for and/or making up the skin, especially of the face (e.g.: a foundation) and the supramolecular polymer(s) may be present therein in a content ranging from 2.5% to 40% by weight of solids relative to the total weight of the composition.

According to an even more preferred variant, a composition is in the form of a composition for caring for and/or making up the skin, especially of the face (e.g.: a foundation) and the supramolecular polymer(s) may be present therein in a content ranging from 3% to 30% by weight of solids relative to the total weight of the composition.

In another particular embodiment of the invention, a composition is in the form of a composition for caring for and/or making up the lips (e.g.: a lipstick) and the supramolecular polymer(s) may be present therein in a content ranging from 0.1% to 60% by weight of solids relative to the total weight of the composition.

According to one preferred variant, a composition is in the form of a composition for caring for and/or making up the lips (e.g.: a lipstick) and the supramolecular polymer(s) may be present therein in a content ranging from 0.2% to 40% by weight of solids relative to the total weight of the composition.

According to an even more preferred variant, a composition is in the form of a composition for caring for and/or making up the lips (e.g.: a lipstick) and the supramolecular polymer(s) may be present therein in a content ranging from 0.5% to 30% by weight of solids relative to the total weight of the composition.

Filler with Absorbing and/or Adsorbing Power

As emerges from the foregoing text, a composition according to the invention comprises at least one filler with capacity for absorbing and/or adsorbing an oil or a liquid fatty substance, for instance sebum (from the skin).

This oil-absorbing filler may also advantageously have a BET specific surface area of greater than or equal to $300 \, m^2/g$, preferably greater than $500 \, m^2/g$ and preferentially greater than $600 \, m^2/g$, and especially less than $1500 \, m^2/g$.

The BET specific surface area is determined according to the BET (Brunauer-Emmet-Teller) method described in the Journal of the American Chemical Society, vol. 60, page 309, February 1938 and corresponding to the international standard ISO 5794/1 (appendix D). The BET specific surface area corresponds to the total specific surface area (thus including micropores) of the powder.

The filler under consideration according to the invention is thus characterized in that it has an oil uptake of greater than or equal to 1.5 ml/g, especially ranging from 1.5 ml/g to 20 ml/g, or even ranging from 1.5 ml/g to 15 ml/g. It preferably has an oil uptake of greater than or equal to 2 ml/g, especially ranging from 2 ml/g to 20 ml/g, or even ranging from 2 ml/g to 15 ml/g.

This oil uptake, which corresponds to the amount of oil absorbed and/or adsorbed by the filler, may be characterized by measuring the wet point according to the method described below.

Method for Measuring the Oil Uptake of a Filler:

The oil uptake of a powder is measured according to the method for determining the oil uptake of a powder described in standard NF T 30-022. It corresponds to the amount of oil adsorbed onto the available surface of the filler, by measuring the wet point.

An amount m (in grams) of powder of between about 0.5 g and 5 g (the amount depends on the density of the powder) is placed on a glass plate and isononyl isononanoate is then added dropwise.

After addition of 4 to 5 drops of isononyl isononanoate, the isononyl isononanoate is incorporated into the filler using a spatula, and addition of the isononyl isononanoate is continued until a conglomerate of isononyl isononanoate and powder has formed. At this point, the isononyl isononanoate is added one drop at a time and the mixture is then triturated with the spatula. The addition of isononyl isononanoate is stopped when a firm, smooth paste is obtained. This paste must be able to be spread on the glass plate without cracking or forming lumps. The volume Vs (expressed in ml) of isononyl isononanoate used is then noted.

The oil uptake corresponds to the ratio Vs/m.

The oil-uptake filler under consideration according to the invention may be of organic or inorganic nature.

The filler may be chosen more particularly from silicas, silica silylates, polyamide (in particular Nylon-6) powders, powders of acrylic polymers, especially of polymethyl methacrylate, of polymethyl methacrylate/ethylene glycol dimethacrylate, of polyallyl methacrylate/ethylene glycol dimethacrylate or of ethylene glycol dimethacrylate/lauryl methacrylate copolymer; perlites; magnesium carbonate, and mixtures thereof.

A person skilled in the art will select among the abovementioned materials fillers with an oil uptake of greater than or equal to 1.5 ml/g and preferably greater than or equal to 2 ml/g, which are in this respect suitable for use in the invention.

Advantageously, the oil-absorbing powder may be a powder coated with a hydrophobic treatment agent.

The hydrophobic treatment agent may be chosen especially from fatty acids such as stearic acid; metal soaps such as aluminium dimyristate, the aluminium salt of hydrogenated tallow glutamate; amino acids; N-acylamino acids or salts thereof; lecithin, isopropyl triisostearyl titanate, mineral waxes, and mixtures thereof.

The N-acylamino acids may comprise an acyl group containing from 8 to 22 carbon atoms, for instance a 2-ethylhexanoyl, caproyl, lauroyl, myristoyl, palmitoyl, stearoyl or cocoyl group. The salts of these compounds may be aluminium, magnesium, calcium, zirconium, zinc, sodium or potassium salts. The amino acid may be, for example, lysine, glutamic acid or alanine.

The term "alkyl" mentioned in the compounds mentioned previously especially denotes an alkyl group containing from 1 to 30 carbon atoms and preferably containing from 5 to 16 carbon atoms.

Examples of fillers in accordance with the invention, i.e. fillers with an oil uptake of greater than or equal to 1.5 ml/g, are described below, with their oil uptake value measured according to the protocol described previously.

Silica powders that may be mentioned include:
porous silica microspheres, especially those sold under the names Sunsphere® H53 and Sunsphere® H33 (oil uptake equal to 3.70 ml/g) by the company Asahi Glass: MSS-500-3H by the company Kobo;
polydimethylsiloxane-coated amorphous silica microspheres, especially those sold under the name SA Sunsphere® H33 (oil uptake equal to 2.43 ml/g),
silica silylate powders, especially those sold under the name Dow Corning VM-2270 Aerogel Fine Particles by the company Dow Corning (oil uptake equal to 10.40 ml/g),
amorphous hollow silica particles, especially those sold under the name Silica Shells by the company Kobo (oil uptake equal to 5.50 ml/g),
precipitated silica powders surface-treated with a mineral wax, such as precipitated silica treated with a polyethylene wax, and especially those sold under the name Acematt OR 412 by the company Evonik-Degussa (oil uptake equal to 3.98 ml/g).

Acrylic polymer powders that may be mentioned include:
porous polymethyl methacrylate/ethylene glycol dimethacrylate spheres sold under the name Microsponge 5640 by the company Cardinal Health Technologies (oil uptake equal to 1.55 ml/g),
ethylene glycol dimethacrylate/lauryl methacrylate copolymer powders, especially those sold under the name Polytrap® 6603 from the company Dow Corning (oil uptake equal to 6.56 ml/g), Polyamide powders that may be mentioned include:
nylon-6 powder, especially the product sold under the name Pomp610 by the company UBE Industries (oil uptake equal to 2.02 ml/g).

A perlite powder that may especially be mentioned is the product sold under the name Optimat 1430 OR by the company World Minerals (oil uptake equal to 2.4 ml/g).

A magnesium carbonate powder that may especially be mentioned is the product sold under the name Tipo Carbomagel by the company Buschle & Lepper (oil uptake equal to 2.14 ml/g).

The oil-absorbing filler that is particularly preferred is a silica powder and more particularly a silica powder with an oil uptake at least equal to 3.70 ml/g, and especially the products sold under the name Sunsphere® H33 by the company Asahi Glass and under the name Dow Corning VM-2270 Aerogel Fine Particles by the company Dow Corning.

Preferably, the oil-absorbing filler used according to the invention is the filler sold under the name Sunsphere® H 33 by the company Asahi Glass. Advantageously, such a filler also makes it possible to fluidize the composition, thus facilitating the application of the composition to the keratin materials.

The filler(s) with an oil uptake of greater than or equal to 1.5 ml/g may be present in a composition according to the invention in a content ranging from 0.5% to 40% by weight, preferably ranging from 1% to 20% by weight and preferentially ranging from 1% to 15% by weight relative to the total weight of the composition.

Advantageously, a composition according to the invention uses at least one filler and at least one supramolecular polymer in a polymer(s)/oil-absorbing filler(s) weight ratio of greater than 1, preferably greater than 1.5 and better still greater than 2.

Additional Fillers

Needless to say, a makeup and/or care composition according to the invention may comprise, besides a filler as defined previously, one or more additional filler(s), i.e. fillers not in accordance with the oil-uptake requirement as defined previously.

According to a first embodiment, the composition is free of additional filler.

According to a second embodiment, the composition comprises at least one additional filler. According to this embodiment, such fillers may be present in a proportion of from 0.01% to 35% by weight and preferably 0.1% to 20% by weight relative to the total weight of the composition. Preferably, a composition according to the invention, when it is in the form of a foundation, comprises at least one additional filler.

Illustrations of these additional fillers that may be mentioned include talc, mica, silica, kaolin, calcium carbonate, barium sulfate, Nylon (especially Orgasol) powder and polyethylene powder, Teflon, starch, boron nitride, copolymer microspheres such as Expancel (Nobel Industrie) and silicone resin microbeads (for example Tospearls from Toshiba); silicone fillers; and also mixtures thereof.

According to one embodiment variant, a composition according to the invention contains at least one filler with an oil uptake of greater than or equal to 1.5 ml/g.

According to another embodiment variant, a composition according to the invention also contains at least one silicone filler.

Silicone Filler

The silicone filler may be chosen from:
organopolysiloxane powders coated with silicone resin; and
polymethylsilsesquioxane powders,
and a mixture thereof.

The organopolysiloxane powder may especially be coated with silsesquioxane resin, as described, for example, in U.S. Pat. No. 5,538,793. Such elastomeric powders are sold under the names KSP-100, KSP-101, KSP-102, KSP-103, KSP-104 and KSP-105 by the company Shin-Etsu, and have the INCI name: vinyl dimethicone/methicone silsesquioxane crosspolymer.

Polymethylsilsesquioxane powders that may especially be mentioned include silicone resin microbeads, such as those sold under the name Tospearl by the company Momentive Performance Materials, and especially under the reference Tospearl 145 A: and mixtures thereof.

In particular, the composition according to the invention may comprise a silicone filler chosen from organopolysiloxane powders coated with silicone resin and polymethylsilsesquioxane powders.

A cosmetic makeup and/or care composition according to the invention also comprises a cosmetically acceptable medium that may comprise the usual ingredients, as a function of the intended use of the composition.

Dyestuff(s)

Preferably, a composition for making up and/or caring for the skin and/or the lips according to the invention comprises at least one dyestuff, in particular at least one pulverulent dyestuff. The dyestuff is especially chosen from organic or mineral dyestuffs, especially such as the pigments or nacres conventionally used in cosmetic compositions, liposoluble or water-soluble dyes, materials with a specific optical effect, and mixtures thereof.

The term "pigments" should be understood as meaning white or coloured, mineral or organic particles, which are insoluble in an aqueous solution and which are intended to colour and/or opacify the resulting film, These pigments may be in the form of powder or of pigmentary paste. They may be coated or uncoated.

As mineral pigments that may be used in the invention, mention may be made of titanium oxide, zirconium oxide or cerium oxide, and also zinc oxide, iron oxide or chromium oxide, ferric blue, manganese violet, ultramarine blue and chromium hydrate. In particular, the mineral pigments are chosen from iron oxides and titanium oxides, and mixtures thereof.

Among the organic pigments that may be used in the invention, mention may be made of carbon black, pigments of D&C type, lakes based on cochineal carmine or on barium, strontium, calcium or aluminium, or alternatively the diketopyrrolopyrroles (DPP) described in documents EP-A-542 669, EP-A-787 730, EP-A-787 731 and WO-A-96/08537.

The term "lake" means dyes adsorbed onto insoluble particles, the assembly thus obtained remaining insoluble during use.

The pigments may also be in the form of composite pigments as described in patent EP 1 184 426. These composite pigments may be especially composed of particles comprising a mineral core, at least one binder for binding the organic pigments to the core, and at least one organic pigment at least partially covering the core.

The term "nacres" should be understood as meaning iridescent or non-iridescent coloured particles of any form, especially produced by certain molluscs in their shell, or else synthesized, and which have a colour effect by optical interference.

The nacres may be chosen from nacreous pigments such as titanium mica coated with an iron oxide, titanium mica coated with bismuth oxychloride, titanium mica coated with chromium oxide, titanium mica coated with an organic dye and also nacreous pigments based on bismuth oxychloride. They may also be mica particles at the surface of which are superposed at least two successive layers of metal oxides and/or of organic dyestuffs.

Examples of nacres that may also be mentioned include natural mica coated with titanium oxide, with iron oxide, with natural pigment or with bismuth oxychloride.

Among the nacres available on the market, mention may be made of the nacres Timica, Flamenco and Duochrome (based on mica) sold by the company Engelhard, the Timiron nacres sold by the company Merck, the Prestige mica-based nacres, sold by the company Eckart, and the Sunshine synthetic mica-based nacres, sold by the company Sun Chemical.

The nacres may more particularly have a yellow, pink, red, bronze, orange, brown, gold and/or coppery colour or tint.

As illustrations of nacres that may be used in the context of the present invention, mention may be made especially of the gold-coloured nacres sold especially by the company Engelhard under the name Brilliant gold 212G (Timica), Gold 222C (Cloisonne), Sparkle gold (Timica), Gold 4504 (Chromalite) and Monarch gold 233X (Cloisonne); the bronze nacres sold especially by the company Merck under the name Bronze fine (17384) (Colorona) and Bronze (17353) (Colorona) and by the company Engelhard under the name Super bronze (Cloisonne); the orange nacres sold especially by the company Engelhard under the name Orange 363C (Cloisonne) and Orange MCR 101 (Cosmica) and by the company Merck under the name Passion orange (Colorona) and Matte orange (17449) (Microna); the brown nacres sold especially by the company Engelhard under the name Nu-antique copper 340XB (Cloisonne) and Brown CL4509 (Chromalite); the nacres with a copper tint sold especially by the company Engelhard under the name Copper 340A (Timica); the nacres with a red tint sold especially by the company Merck under the name Sienna fine (17386) (Colorona); the nacres with a yellow tint sold especially by the company Engelhard under the name Yellow (4502) (Chromalite); the red nacres with a gold tint sold especially by the company Engelhard under the name Sunstone G012 (Gemtone); the pink nacres sold especially by the company Engelhard under the name Tan opale G005 (Gemtone); the black nacres with a gold tint sold especially by the company Engelhard under the name Nu antique bronze 240 AB (Timica), the blue nacres sold especially by the company Merck under the name Matte blue (17433) (Microna), the white nacres with a silvery tint sold especially by the company Merck under the name Xirona Silver, and the golden-green pink-orange nacres sold especially by the company Merck under the name Indian summer (Xirona), and mixtures thereof.

The cosmetic composition according to the invention may also comprise water-soluble or liposoluble dyes. The term "dyes" should be understood as meaning compounds that are generally organic, which are soluble in fatty substances such as oils or in an aqueous-alcoholic phase. The liposoluble dyes are, for example, Sudan red, DC Red 17, DC Green 6, β-carotene, soybean oil, Sudan brown, DC Yellow 11, DC Violet 2, DC Orange 5 and quinoline yellow. The water-soluble dyes are, for example, beetroot juice and caramel.

The cosmetic composition according to the invention may also contain at least one material with a specific optical effect.

This effect is different than a simple conventional hue effect, i.e. a unified and stabilized effect as produced by standard dyestuffs, for instance monochromatic pigments.

For the purposes of the invention, the term "stabilized" means lacking an effect of variability of the colour as a function of the angle of observation or alternatively in response to a temperature change.

For example, this material may be chosen from particles with a metallic tint, goniochromatic colouring agents, diffracting pigments, thermochromic agents, optical brighteners, and also fibres, especially interference fibres. Needless to say, these various materials may be combined so as to afford the simultaneous manifestation of two effects, or even of a novel effect in accordance with the invention.

The particles with a metallic tint that may be used in the invention are chosen in particular from:
particles of at least one metal and/or of at least one metal derivative.
particles comprising a mono-material or multi-material organic or mineral substrate, at least partially coated with at least one coat with a metallic tint comprising at least one metal and/or at least one metal derivative, and mixtures of the said particles.

Among the metals that may be present in the said particles, mention may be made, for example, of Ag, Au, Cu, Al, Ni, Sn, Mg, Cr, Mo, Ti, Zr, Pt, Va, Rb, W, Zn, Ge, Te and Se, and mixtures or alloys thereof. Ag, Au, Cu, Al, Zn, Ni, Mo and Cr and mixtures or alloys thereof (for example bronzes and brasses) are preferred metals.

Illustrations of these particles that may be mentioned include aluminium particles, such as those sold under the names Starbrite 1200 EAC® by the company Siberline and Metalure® by the company Eckart.

Mention may also be made of copper metal powders or alloy mixtures such as the reference 2844 sold by the company Radium Bronze, metallic pigments such as aluminium or bronze, such as those sold under the name Rotosafe 700 from the company Eckart, the silica-coated aluminium particles sold under the name Visionaire Bright Silver from the company Eckart and metal alloy particles, for instance the silica-coated bronze (alloy of copper and zinc) powders sold under the name Visionaire Bright Natural Gold from the company Eckart.

They may also be particles comprising a glass substrate, such as those sold by the company Nippon Sheet Glass under the name Microglass Metashine.

The goniochromatic colouring agent may be chosen, for example, from interference multilayer structures and liquid-crystal colouring agents.

Examples of symmetrical interference multilayer structures that may be used in compositions produced in accordance with the invention are, for example, the following structures: $Al/SiO_2/Al/SiO_2/Al$, pigments having this structure being sold by the company Dupont de Nemours; $Cr/MgF_2/Al/MgF_2/Cr$, pigments having this structure being sold under the name Chromaflair by the company Flex; $MoS_2/SiO_2/Al/SiO_2/MoS_2$; $Fe_2O_3/SiO_2/Al/SiO_2/Fe_2O_3$, and $Fe_2O_3/SiO_2/Fe_2O_3$, pigments having these structures being sold under the name Sicopearl by the company BASF; $MoS_2/SiO_2/mica$-oxide$/SiO_2/MoS_2$; $Fe_2O_3/SiO_2/mica$-oxide$/SiO_2/Fe_2O_3$; $TiO_2/SiO_2/TiO_2$ and $TiO_2/Al_2O_3/TiO_2$: $SnO/TiO_2/SiO_2/TiO_2/SnO$; $Fe_2O_3/SiO_2/Fe_2O_3$; $SnO/mica/TiO_2/SiO_2/TiO_2/mica/SnO$, pigments having these structures being sold under the name Xirona by the company Merck (Darmstadt). By way of example, these pigments may be the pigments of silica/titanium oxide/tin oxide structure sold under the name Xirona Magic by the company Merck, the pigments of silica/brown iron oxide structure sold under the name Xirona Indian Summer by the company Merck and the pigments of silica/titanium oxide/mica/tin oxide structure sold under the name Xirona Caribbean Blue by the company Merck. Mention may also be made of the Infinite Colors pigments from the company Shiseido. Depending on the thickness and the nature of the various coats, different effects are obtained. Thus, with the $Fe_2O_3/SiO_2/Al/SiO_2/Fe_2O_3$ structure, the colour changes from green-golden to red-grey for $SiO_2$ layers of 320 to 350 nm; from red to golden for $SiO_2$ layers of 380 to 400 nm; from violet to green for $SiO_2$ layers of 410 to 420 nm; from copper to red for $SiO_2$ layers of 430 to 440 nm.

Examples of pigments with a polymeric multilayer structure that may be mentioned include those sold by the company 3M under the name Color Glitter.

Examples of liquid-crystal goniochromatic particles that may be used include those sold by the company Chenix and also the product sold under the name Helicone®HC by the company Wacker.

Preferably, the amount of dyestuffs in a composition according to the invention is between 0.01% and 40% by weight and especially between 0.1% and 30% by weight, or even between 1% and 20% by weight relative to the total weight of the composition.

Fatty Phase

A composition according to the invention may comprise a fatty phase, which may represent from 1% to 98% by weight, especially 5% to 95% by weight or even 10% to 90% by weight relative to the total weight of the composition. This fatty phase may comprise oils, waxes and/or pasty compounds and/or silicone compounds as defined below.

The oils, preferably silicone oils, and/or silicone compounds may be present in a proportion ranging from 0.1% to 60% by weight and preferably from 0.5% to 40% by weight relative to the total weight of the composition.

Thus, a composition according to the invention may advantageously comprise one or more oils, which may be chosen especially from hydrocarbon-based oils and fluoro oils, and mixtures thereof. The oils may be of animal, plant, mineral or synthetic origin.

The term "oil" means a water-immiscible non-aqueous compound that is liquid at room temperature (25° C.) and at atmospheric pressure (760 mmHg).

The oils may be volatile or non-volatile.

For the purposes of the invention, the term "volatile oil" means any oil that is capable of evaporating on contact with keratin materials in less than one hour, at room temperature and atmospheric pressure. Volatile oils preferably have a non-zero vapour pressure, at room temperature and atmospheric pressure, ranging from 0.13 Pa to 40 000 Pa, in particular from 1.3 Pa to 13 000 Pa and more particularly from 1.3 Pa to 1300 Pa.

The term "fluoro oil" means an oil comprising at least one fluorine atom.

The term "hydrocarbon-based oil" means an oil mainly containing hydrogen and carbon atoms.

The oils may optionally comprise oxygen, nitrogen, sulfur and/or phosphorus atoms, for example in the form of hydroxyl or acid radicals.

The volatile oils may be chosen from hydrocarbon-based oils containing from 8 to 16 carbon atoms, and especially $C_8$-$C_{16}$ branched alkanes (also known as isoparaffins), for instance isododecane, isodecane and isohexadecane.

The volatile hydrocarbon-based oil may also be a linear volatile alkane containing 7 to 17 carbon atoms, in particular 9 to 15 carbon atoms and more particularly 11 to 13 carbon atoms. Mention may be made especially of n-nonadecane, n-decane, n-undecane, n-dodecane, n-tridecane, n-tetradecane, n-pentadecane and n-hexadecane, and mixtures thereof.

Non-volatile oils that may especially be mentioned include:

hydrocarbon-based oils of animal origin,
hydrocarbon-based oils of plant origin, such as phytostearyl esters, such as phytostearyl oleate, phytostearyl isostearate and lauroyl/octyldodecyl/phytostearyl glutamate: triglycerides formed from fatty acid esters of glycerol, in particular whose fatty acids may have chain lengths ranging from $C_4$ to $C_{36}$ and especially from $C_{18}$ to $C_{36}$, these oils possibly being linear or branched, and saturated or unsaturated; these oils may especially be heptanoic or octanoic triglycerides, shea oil, alfalfa oil, poppy oil, pumpkin oil, millet oil, barley oil, quinoa oil, rye oil, candlenut oil, passionflower oil, shea butter oil, aloe oil, sweet almond oil, peach stone oil, groundnut oil, argan oil, avocado oil, baobab oil, borage oil, broccoli oil, calendula oil, camellina oil, carrot oil, safflower oil, hemp oil, rapeseed oil, cottonseed oil, coconut oil, marrow seed oil, wheatgerm oil, jojoba oil, lily oil, macadamia oil, corn oil, meadowfoam oil, St-John's wort oil, monoi oil, hazelnut oil, apricot kernel oil, walnut oil, olive oil, evening primrose oil, palm oil, blackcurrant pip oil, kiwi seed oil, grape seed oil, pistachio oil, pumpkin oil, quinoa oil, musk rose oil, sesame oil, soybean oil, sunflower oil, castor oil and watermelon oil, and mixtures thereof, or alternatively caprylic/capric acid triglycerides, such as those sold by the company Stearineries Dubois or those sold under the names Miglyol 810®, 812® and 818® by the company Dynamit Nobel,
synthetic ethers containing from 10 to 40 carbon atoms;
synthetic esters, for instance the oils of formula $R_1COOR_2$, in which $R_1$ represents a linear or branched fatty acid residue containing from 1 to 40 carbon atoms and $R_2$ represents a hydrocarbon-based chain, which is especially branched, containing from 1 to 40 carbon atoms, on condition that $R_1+R_2 \geq 10$. The esters may be chosen especially from fatty acid esters of alcohols, for instance cetostearyl octanoate, isopropyl alcohol esters, such as isopropyl myristate, isopropyl palmitate, ethyl palmitate, 2-ethylhexyl palmitate, isopropyl stearate, isopropyl isostearate, isostearyl isostearate, octyl stearate, hydroxylated esters, for instance isostearyl lactate, octyl hydroxystearate, diisopropyl adipate, heptanoates, and especially isostearyl heptanoate, alcohol or polyalcohol octanoates, decanoates or ricinoleates, for instance propylene glycol dioctanoate, cetyl octanoate, tridecyl octanoate, 2-ethylhexyl 4-diheptanoate, 2-ethylhexyl palmitate, alkyl benzoates, polyethylene glycol diheptanoate, propylene glycol 2-diethylhexanoate, and mixtures thereof, $C_{12}$-$C_{15}$ alcohol benzoates, hexyl laurate, neopentanoic acid esters, for instance isodecyl neopentanoate, isotridecyl neopentanoate, isostearyl neopentanoate, octyldodecyl neopentanoate, isononanoic acid esters, for instance isononyl isononanoate, isotridecyl isononanoate, octyl isononanoate, hydroxylated esters, for instance isostearyl lactate and diisostearyl malate,
polyol esters and pentaerythritol esters, for instance dipentaerythrityl tetrahydroxystearate/tetraisostearate.
esters of diol dimers and of diacid dimers,
copolymers of diol dimer and of diacid dimer and esters thereof, such as dilinoleyl diol dimer/dilinoleic dimer copolymers, and esters thereof,
copolymers of polyols and of diacid dimers, and esters thereof,
fatty alcohols that are liquid at room temperature, with a branched and/or unsaturated carbon-based chain containing from 12 to 26 carbon atoms, for instance 2-octyldodecanol, isostearyl alcohol, oleyl alcohol, 2-hexyldecanol, 2-butyloctanol and 2-undecylpentadecanol, $C_{12}$-$C_{22}$ higher fatty acids, such as oleic acid, linoleic acid and linolenic acid, and mixtures thereof;

dialkyl carbonates, the two alkyl chains possibly being identical or different, such as dicaprylyl carbonate;

oils with a molar mass of between about 400 and about 10 000 g/mol, in particular about 650 to about 10 000 g/mol, in particular from about 750 to about 7500 g/mol and more particularly ranging from about 1000 to about 5000 g/mol; mention may be made especially, alone or as a mixture, of (i) lipophilic polymers such as polybutylenes, polyisobutylenes, for example hydrogenated, polydecenes and hydrogenated polydecenes, vinylpyrrolidone copolymers, such as the vinylpyrrolidone/1-hexadecene copolymer, and polyvinylpyrrolidone (PVP) copolymers, such as the copolymers of a $C_2$-$C_{30}$ alkene, such as $C_3$-$C_{22}$, and combinations thereof; (ii) linear fatty acid esters containing a total carbon number ranging from 35 to 70, for instance pentaerythrityl tetrapelargonate; (iii) hydroxylated esters such as polyglyceryl-2 triisostearate; (iv) aromatic esters such as tridecyl trimellitate; (v) esters of fatty alcohols or of branched $C_{24}$-$C_{28}$ fatty acids, such as those described in U.S. Pat. No. 6,491,927 and pentaerythritol esters, and especially triisoarachidyl citrate, pentaerythrityl tetraisononanoate, glyceryl triisostearate, glyceryl 2-tridecyltetradecanoate, pentaerythrityl tetraisostearate, poly (2-glyceryl)tetraisostearate or pentaerythrityl 2-tetradecyltetradecanoate; (vi) diol dimer esters and polyesters, such as esters of diol dimer and of fatty acid, and esters of diol dimer and of diacid.

In particular, one or more oils according to the invention may be present in a composition according to the invention in a content ranging from 1% to 90% by weight, preferably ranging from 2% to 75% by weight or even from 3% to 60% by weight relative to the total weight of the composition.

It is understood that this weight percentage of oil takes into account the weight of oil used for the formulation of the associated supramolecular polymer, if present.

Silicone Compound

As stated above, a composition according to the invention may comprise at least one silicone compound with a viscosity of less than 10 000 000 cSt at 25° C. Such a compound is advantageously chosen from silicone gums, volatile silicone oils and non-volatile silicone oils.

In particular, the silicone compound under consideration according to the invention may be a silicone oil with a viscosity of between 3 centistokes (cSt) ($3×10^{-6}$ m²/s) and 800 000 centistokes (cSt) ($800\,000×10^{-6}$ m²/s).

Preferably, the silicone compound under consideration according to the invention may be a non-volatile silicone oil with a viscosity of between 9 centistokes (cSt) ($9×10^{-6}$ m²/s) and 600 000 centistokes (cSt) ($600\,000×10^{-6}$ m²/s).

Silicone Oils

For the purposes of the present invention, the term "silicone oil" means an oil comprising at least one silicon atom, and especially at least one Si—O group.

In particular, the volatile or non-volatile silicone oils that may be used in the invention preferably have a viscosity at 25° C. of less than 800 000 cSt, preferably less than or equal to 600 000 cSt and preferably less than or equal to 500 000 cSt. The viscosity of these silicone oils may be measured according to standard ASTM D-445.

As emerges from the foregoing text, a composition according to the invention and/or under consideration according to a process of the invention contains at least one silicone oil other than cyclopentasiloxane. Such an oil, also known as decamethylcyclopentasiloxane, is especially sold under the name DC-245 by the company Dow Corning or Mirasil CM 5.

Needless to say, a composition according to the invention or under consideration according to a process of the invention may contain a mixture of silicone oils formed only partly from such an oil.

The silicone oils that may be used according to the invention may be volatile and/or non-volatile.

Thus, a composition according to the invention or under consideration according to a process of the invention may contain a mixture of volatile and non-volatile silicone oil.

The term "volatile oil" means an oil that can evaporate on contact with the skin in less than one hour, at room temperature (25° C.) and atmospheric pressure. The volatile oil is a volatile cosmetic oil, which is liquid at room temperature, especially having a non-zero vapour pressure, at room temperature and atmospheric pressure, in particular having a vapour pressure ranging from 0.13 Pa to 40 000 Pa ($10^{-3}$ to 300 mmHg), preferably ranging from 1.3 Pa to 13 000 Pa (0.01 to 100 mmHg) and preferentially ranging from 1.3 Pa to 1300 Pa (0.1 to 10 mmHg).

The term "non-volatile oil" means an oil whose vapour pressure at room temperature and atmospheric pressure is non-zero and less than 0.02 mmHg (2.66 Pa) and better still less than $10^{-3}$ mmHg (0.13 Pa).

Volatile Silicone Oils

According to a first embodiment, the compositions according to the invention comprise at least one volatile silicone oil.

The volatile silicone oils that may be used in the invention may be chosen from silicone oils especially having a viscosity ≥8 centistokes (cSt) ($8×10^{-6}$ m²/s at 25° C.).

Furthermore, the volatile silicone oil that may be used in the invention may preferably be chosen from silicone oils with a flash point ranging from 40° C. to 102° C., preferably with a flash point of greater than 55° C. and less than or equal to 95° C., and preferentially ranging from 65° C. to 95° C.

Volatile silicone oils that may be mentioned include:

volatile linear or cyclic silicone oils, especially those with a viscosity ≤8 centistokes (cSt) ($8×10^{-6}$ m²/s at 25° C.), and especially containing from 2 to 10 silicon atoms and in particular from 2 to 7 silicon atoms, these silicones optionally comprising alkyl or alkoxy groups containing from 1 to 10 carbon atoms.

More particularly, the volatile silicone oils are non-cyclic and are chosen in particular from:

the non-cyclic linear silicones of formula (I):

$$R_3SiO\text{—}(R_2SiO)_n\text{—}SiR_3 \tag{I}$$

in which R, which may be identical or different, denotes:

a saturated or unsaturated hydrocarbon-based radical, containing from 1 to 10 carbon atoms and preferably from 1 to 6 carbon atoms, optionally substituted with one or more fluorine atoms or with one or more hydroxyl groups, or a hydroxyl group, one of the radicals R possibly being a phenyl group, n is an integer ranging from 0 to 8, preferably ranging from 2 to 6 and better still ranging from 3 to 5, the silicone compound of formula (I) containing not more than 15 carbon atoms, the branched silicones of formula (II) or (III) below:

$$R_3SiO\text{—}[(R_3SiO)RSiO]\text{—}(R_2SiO)_x\text{—}SiR_3 \tag{II}$$

$$[R_3SiO]4Si \tag{III}$$

in which R, which may be identical or different, denotes:
a saturated or unsaturated hydrocarbon-based radical, containing from 1 to 10 carbon atoms, optionally substituted with one or more fluorine atoms or with one or more hydroxyl groups, or
a hydroxyl group, one of the radicals R possibly being a phenyl group, x is an integer ranging from 0 to 8, the silicone compound of formula (II) or (III) containing not more than 15 carbon atoms.

Preferably, for the compounds of formulae (I), (II) and (III), the ratio between the number of carbon atoms and the number of silicon atoms is between 2.25 and 4.33.

The silicones of formulae (I) to (III) may be prepared according to the known processes for synthesizing silicone compounds.

Among the silicones of formula (I) that may be mentioned are:
the following disiloxanes: hexamethyldisiloxane (surface tension=15.9 mN/m), sold especially under the name DC 200 Fluid 0.65 cSt by the company Dow Corning, 1,3-di-tert-butyl-1,1,3,3-tetramethyldisiloxane; 1,3-dipropyl-1,1,3,3-tetramethyldisiloxane; heptylpentamethyldisiloxane; 1,1,1-triethyl-3,3,3-trimethyldisiloxane; hexaethyldisiloxane; 1,1,3,3-tetramethyl-1,3-bis (2-methylpropyl)disiloxane; pentamethyloctyldisiloxane; 1,1,1-trimethyl-3,3,3-tris(1-methylethyl)disiloxane; 1-butyl-3-ethyl-1,1,3-trimethyl-3-propyldisiloxane; pentamethylpentyldisiloxane: 1-butyl-1,1,3,3-tetramethyl-3-(1-methylethyl) disiloxane; 1,1,3,3-tetramethyl-1,3-bis(1-methylpropyl)disiloxane; 1,1,3-triethyl-1,3,3-tripropyldisiloxane; (3,3-dimethylbutyl) pentamethyldisiloxane; (3-methylbutyl) pentamethyldisiloxane; (3-methylpentyl) pentamethyldisiloxane; 1,1,1-triethyl-3,3-dimethyl-3-propyldisiloxane: 1-(1,1-dimethylethyl)-1,1,3,3,3-pentamethyldisiloxane; 1,1,1-trimethyl-3,3,3-tripropyldisiloxane; 1,3-dimethyl-1,1,3,3-tetrakis(1-methylethyl)disiloxane; 1,1-dibutyl-1,3,3,3-tetramethyldisiloxane: 1,1,3,3-tetramethyl-1,3-bis(1-methylethyl)disiloxane; 1,1,3-tetramethyl-3,3-bis(1-methylethyl)disiloxane; 1,1,1,3-tetramethyl-3,3-dipropyldisiloxane; 1,1,3,3-tetramethyl-1,3-bis(3-methylbutyl)disiloxane; butylpentamethyldisiloxane; pentaethylmethyldisiloxane; 1,1,3,3-tetramethyl-1,3-dipentyldisiloxane; 1,3-dimethyl-1,1,3,3-tetrapropyldisiloxane; 1,1,1,3-tetraethyl-3,3-dimethyldisiloxane; 1,1,1-triethyl-3,3,3-tripropyldisiloxane; 1,3-dibutyl-1,1,3,3-tetramethyldisiloxane and hexylpentamethyldisiloxane;
the following trisiloxanes: octamethyltrisiloxane (surface tension=17.4 mN/m), sold especially under the name DC 200 Fluid 1 cSt by the company Dow Corning, 3-pentyl-1,1,1,3,5,5,5-heptamethyltrisiloxane: 1-hexyl-1,1,3,3,5,5,5-heptamethyltrisiloxane; 1,1,1,3,3,5,5-heptamethyl5-octyltrisiloxane; 1,1,1,3,5,5,5-heptamethyl-3-octyltrisiloxane, sold especially under the name Silsoft 034 by the company OSI; 1,1,1,3,5,5,5-heptamethyl-3-hexyltrisiloxane (surface tension=20.5 mN/m), sold especially under the name DC 2-1731 by the company Dow Corning; 1,1,3,3,5,5-hexamethyl-1,5-dipropyltrisiloxane; 3-(1-ethylbutyl)-1,1,1,3,5,5,5-heptamethyltrisiloxane; 1,1,1,3,5,5,5-heptamethyl-3-(1-methylpentyl)trisiloxane; 1,5-diethyl-1,1,3,3,5,5-hexamethyltrisiloxane; 1,1,1,3,5,5,5-heptamethyl-3-(1-methylpropyl)trisiloxane; 3-(1,1-dimethylethyl)-1,1,1,3,5,5,5-heptamethyltrisiloxane; 1,1,1,5,5,5-hexamethyl-3,3-bis(1-methylethyl)trisiloxane; 1,1,1,3,3,5,5-hexamethyl-1,5-bis(1-methylpropyl)trisiloxane: 1,5-bis(1,1-dimetethylethyl)-1,1,3,3,5,5-hexamethyltrisiloxane; 3-(3,3-dimethylbutyl)-1,1,1,3,5,5,5-heptamethyltrisiloxane; 1,1,1,3,5,5,5-heptamethyl-3-(3-methylbutyl)trisiloxane; 1,1,1,3,5,5,5-heptamethyl-3-(3-methylpentyl)trisiloxane; 1,1,1,3,5,5,5-heptamethyl-3-(2-methylpropyl)trisiloxane; 1-butyl-1,1,3,3,5,5,5-heptamethyltrisiloxane; 1,1,1,3,5,5,5-heptamethyl-3-propyltrisiloxane; 3-isohexyl-1,1,1,3,5,5,5-heptamethyltrisiloxane; 1,3,5-triethyl-1,1,3,5,5,5-pentamethyltrisiloxane: 3-butyl-1,1,1,3,5,5,5-heptamethyltrisiloxane; 3-tert-pentyl-1,1,1,3,5,5,5-heptamethyltrisiloxane; 1,1,1,5,5,5-hexamethyl-3,3-dipropyltrisiloxane: 3,3-diethyl-1,1,1,5,5,5-hexamethyltrisiloxane; 1,5-dibutyl-1,1,3,3,5,5-hexamethyltrisiloxane; 1,1,1,5,5,5-hexaethyl-3,3-dimethyltrisiloxane; 3,3-dibutyl-1,1,1,5,5,5-hexamethyltrisiloxane; 3-ethyl-1,1,1,3,5,5,5-heptamethyltrisiloxane; 3-heptyl-1,1,1,3,5,5,5-heptamethyltrisiloxane and 1-ethyl-1,1,3,5,5,5-heptamethyltrisiloxane;
the following tetrasiloxanes: decamethyltetrasiloxane (surface tension=18 mN/m), sold especially under the name DC 200 Fluid 1.5 cSt by the company Dow Corning; 1,1,3,3,5,5,7,7-octamethyl-1,7-dipropyltetrasiloxane; 1,1,1,3,3,5,7,7,7-nonamethyl-5-(1-methylethyl)tetrasiloxane; 1-butyl-1,1,3,3,5,5,7,7,7-nonamethyltetrasiloxane; 3,5-diethyl-1,1,1,3,5,7,7,7-octamethyltetrasiloxane; 1,3,5,7-tetraethyl-1,1,3,5,7,7-hexamethyltetrasiloxane; 3,3,5,5-tetraethyl-1,1,1,7,7,7-hexamethyltetrasiloxane; 1,1,1,3,3,5,5,7,7-nonamethyl-7-phenyltetrasiloxane; 3,3-diethyl-1,1,1,5,5,7,7,7-octamethyltetrasiloxane; 1,1,3,3,5,7,7,7-nonamethyl-5-phenyltetrasiloxane:
the following pentasiloxanes: dodecamethylpentasiloxane (surface tension=18.7 mN/m), sold especially under the name DC 200 Fluid 2 cSt by the company Dow Corning; 1,1,3,3,5,5,7,7,9,9-decamethyl-1,9-dipropylpentasiloxane; 3,3,5,5,7,7-hexaethyl-1,1,1,9,9,9-hexamethylpentasiloxane; 1,1,1,3,3,5,7,7,9,9,9-undecamethyl-5-phenylpentasiloxane; 1-butyl-1,1,3,3,5,5,7,7,9,9,9-undecamethylpentasiloxane; 3,3-diethyl-1,1,1,5,5,7,7,9,9,9-decamethylpentasiloxane; 1,3,5,7,9-pentaethyl-1,1,3,5,7,9,9-heptamethylpentasiloxane; 3,5,7-triethyl-1,1,1,3,5,7,9,9,9,9-nonamethylpentasiloxane and 1,1,1-triethyl-3,3,5,5,7,7,9,9,9-nonamethylpentasiloxane;
the following hexasiloxanes: 1-butyl-1,1,3,3,5,5,7,7,9,9,11,11,11-tridecamethylhexasiloxane; 3,5,7,9-tetraethyl-1,1,1,3,5,7,9,11,11,11-decamethylhexasiloxane and tetradecamethylhexasiloxane.
hexadecamethylheptasiloxane;
octadecamethyloctasiloxane:
eicosamethylnonasiloxane.

Among the silicones of formula (II) that may be mentioned are:
the following tetrasiloxanes: 2-[3,3,3-trimethyl-1,1-bis [(trimethyl silyl)oxy]disiloxanyl]ethyl; 1,1,1,5,5,5-hexamethyl-3-(2-methylpropyl)-3-[(trimethylsilyl)oxy] trisiloxane; 3-(1,1-dimethylethyl)-1,1,1,5,5,5-hexamethyl-3-[(trimethylsilyl)oxy]trisiloxane; 3-butyl-1,1,1,5,5,5-hexamethyl-3-[(trimethylsilyl)oxy] trisiloxane; 1,1,1,5,5,5-hexamethyl-3-propyl-3-[(trimethylsilyl)oxy]trisiloxane; 3-ethyl-1,1,1,5,5,5-hexamethyl-3-[(trimethylsilyl)oxy]trisiloxane; 1,1,1-triethyl-3,5,5,5-tetramethyl-3-(trimethylsiloxy)trisiloxane; 3-methyl-1,1,1,5,5,5-hexamethyl-3-

[trimethylsilyl)oxy]trisiloxane; 3-[(dimethylphenylsilyl)oxy]-1,1,1,3,5,5,5-heptamethyltrisiloxane; 1,1,1,5,5,5-hexamethyl-3-(2-methylpentyl)-3-[(trimethylsilyl)oxy]trisiloxane; 1,1,1,5,5,5-hexamethyl-3-(4-methylpentyl)-3-[(trimethylsilyl)oxy] trisiloxane; 3-hexyl-1,1,1,5,5,5-hexamethyl-3-[(trimethylsilyl)oxy]trisiloxane and 1,1,1,3,5,5,5-heptamethyl-3-[(trimethylsilyl)oxy]trisiloxane;

the following pentasiloxanes: 1,1,1,3,5,5,7,7,7-nonamethyl-3-(trimethylsiloxy)tetrasiloxane and 1,1,1,3,3,7,7,7-octamethyl-5-phenyl-5-[(trimethylsilyl)oxy]tetrasiloxane;

the following heptasiloxane: 1,1,1,3,5,5,7,7,9,9,11,11,11-tridecamethyl-3-[(trimethylsilyl)oxy]hexasiloxane.

Among the silicones of formula (III), mention may be made of:

1,1,1,5,5,5-hexamethyl-3,3-bis(trimethylsiloxy)trisiloxane.

Use may also be made of other volatile silicone oils chosen from:

the following tetrasiloxanes: 2,2,8,8-tetramethyl-5-[(pentamethyldisiloxanyl)methyl]-3,7-dioxa-2,8-disilanonane; 2,2,5,8,8-pentamethyl-5-[(trimethylsilyl)methoxy]-4,6-dioxa-2,5,8-trisilanonane; 1,3-dimethyl-1,3-bis[(trimethylsilyl)methyl]-1,3-disiloxanediol; 3-ethyl-1,1,1,5,5,5-hexamethyl-3-[3-(trimethylsiloxy)propyl]trisiloxane and 1,1,5,5,5-hexamethyl-3-phenyl-3-[(trimethylsilyl)oxy]trisiloxane (Dow 556 Fluid);

the following pentasiloxanes: 2,2,7,7,9,9,11,11,16,16-decamethyl-3,8,10,15-tetraoxa-2,7,9,11,16-pentasilaheptadecane and the tetrakis[(trimethylsilyl)methyl]ester of silicic acid;

the following hexasiloxanes: 3,5-diethyl-1,1,1,7,7,7-hexamethyl-3,5-bis[(trimethylsilyl)oxy]tetrasiloxane and 1,1,1,3,5,7,7,7-octamethyl-3,5-bis[(trimethylsilyl)oxy]tetrasiloxane:

the heptasiloxane: 1,1,1,3,7,7,7-heptamethyl-3,5,5-tris[(trimethylsilyl)oxy]tetrasiloxane;

the following octasiloxanes: 1,1,1,3,5,5,9,9,9-nonamethyl-3,7,7-tris[(trimethylsilyl)oxy]pentasiloxane; 1,1,1,3,5,7,9,9,9-nonamethyl-3,5,7-tris[(trimethylsilyl)oxy]pentasiloxane and 1,1,1,7,7,7-hexamethyl-3,3,5,5-tetrakis[(trimethylsilyl)oxy]tetrasiloxane.

Volatile silicone oils that may more particularly be mentioned include decamethyl cyclopentasiloxane sold especially under the name DC-245 by the company Dow Corning, dodecamethylcyclohexasiloxane sold especially under the name DC-246 by the company Dow Corning, octamethyltrisiloxane sold especially under the name DC-200 Fluid 1 cSt by the company Dow Corning, decamethyltetrasiloxane sold especially under the name DC-200 Fluid 1.5 cSt by the company Dow Corning and DC-200 Fluid 5 cSt sold by the company Dow Corning, octamethylcyclotetrasiloxane, heptamethylhexyltrisiloxane, heptamethylethyltrisiloxane, heptamethyloctyltrisiloxane and dodecamethylpentasiloxane, and mixtures thereof.

It should be noted that, among the abovementioned oils, the linear oils prove to be particularly advantageous.

Non-Volatile Silicone Oils

According to a second embodiment, the compositions according to the invention comprise at least one non-volatile silicone oil.

The non-volatile silicone oils that may be used in the invention may be chosen from silicone oils with a viscosity at 25° C. of greater than or equal to 9 centistokes (cSt) ($9\times10^{-6}$ m$^2$/s) and less than 800 000 cSt, preferably between 50 and 600 000 cSt and preferably between 100 and 500 000 cSt. The viscosity of this silicone oil may be measured according to standard ASTM D-445.

Among these silicone oils, two types of oil may be distinguished, according to whether or not they contain phenyl.

Representative examples of these non-volatile linear silicone oils that may be mentioned include polydimethylsiloxanes; alkyl dimethicones; vinyl methyl methicones; and also silicones modified with optionally fluorinated aliphatic groups, or with functional groups such as hydroxyl, thiol and/or amine groups.

Thus, non-phenyl non-volatile silicone oils that may be mentioned include:

PDMSs comprising alkyl or alkoxy groups, which are pendent and/or at the end of the silicone chain, these groups each containing from 2 to 24 carbon atoms, PDMSs comprising aliphatic groups, or functional groups such as hydroxyl, thiol and/or amine groups, polyalkylmethylsiloxanes optionally substituted with a fluorinated group, such as polymethyltrifluoropropyldimethylsiloxanes, polyalkylmethylsiloxanes substituted with functional groups such as hydroxyl, thiol and/or amine groups, polysiloxanes modified with fatty acids, fatty alcohols or polyoxyalkylenes, and mixtures thereof.

According to one embodiment, a composition according to the invention contains at least one non-phenyl linear silicone oil.

The non-phenyl linear silicone oil may be chosen especially from the silicones of formula:

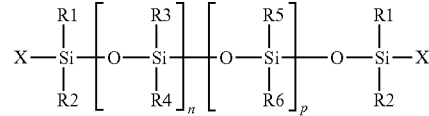

in which:

$R_1$, $R_2$, $R_5$ and $R_6$ are, together or separately, an alkyl radical containing 1 to 6 carbon atoms, $R_3$ and $R_4$ are, together or separately, an alkyl radical containing from 1 to 6 carbon atoms, a vinyl radical, an amine radical or a hydroxyl radical, X is an alkyl radical containing from 1 to 6 carbon atoms, a hydroxyl radical or an amine radical, n and p are integers chosen so as to have a fluid compound.

As non-volatile silicone oils that may be used according to the invention, mention may be made of those for which:

the substituents $R_1$ to $R_6$ and X represent a methyl group, and p and n are such that the viscosity is 500 000 cSt, such as the product sold under the name SE30 by the company General Electric, the product sold under the name AK 500000 by the company Wacker, the product sold under the name Mirasil DM 500 000 by the company Bluestar, and the product sold under the name Dow Corning 200 Fluid 500 000 cSt by the company Dow Corning, the substituents $R_1$ to $R_6$ and X represent a methyl group, and p and n are such that the viscosity is 60 000 cSt, such as the product sold under the name Dow Corning 200 Fluid 60000 CS by the company Dow Corning, and the product sold under the name Wacker Belsil DM 60 000 by the company Wacker, the substituents $R_1$ to $R_6$ and X represent a methyl group, and p and n are such that the viscosity is 350 cSt, such as the product sold under the name Dow Corning 200 Fluid 350 CS by the company Dow Corning, the substituents $R_1$ to $R_6$ represent a methyl group, the group X represents a hydroxyl group, and n and p are such that the viscosity is 700 cSt, such as the product sold under the name Baysilone Fluid T0.7 by the company Momentive.

According to one embodiment variant, a composition according to the invention contains at least one phenyl silicone oil.

Representative examples of these non-volatile phenyl silicone oils that may be mentioned include:

the phenyl silicone oils corresponding to the following formula:

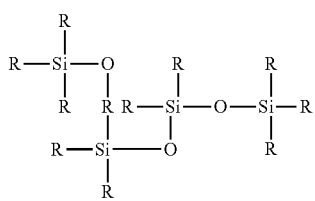

(I)

in which the groups R represent, independently of each other, a methyl or a phenyl, with the proviso that at least one group R represents a phenyl. Preferably, in this formula, the phenyl silicone oil comprises at least three phenyl groups, for example at least four, at least five or at least six.

the phenyl silicone oils corresponding to the following formula:

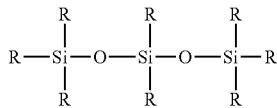

(II)

in which the groups R represent, independently of each other, a methyl or a phenyl, with the proviso that at least one group R represents a phenyl. Preferably, in this formula, the said organopolysiloxane comprises at least three phenyl groups, for example at least four or at least five. Mixtures of the phenyl organopolysiloxanes described previously may be used. Examples that may be mentioned include mixtures of triphenyl, tetraphenyl or pentaphenyl organo-polysiloxanes.

the phenyl silicone oils corresponding to the following formula:

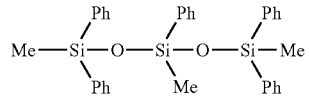

(III)

in which Me represents methyl, Ph represents phenyl. Such a phenyl silicone is especially manufactured by Dow Corning under the reference PH-1555 HRI or Dow Corning 555 Cosmetic Fluid (chemical name: 1,3,5-trimethyl-1,1,3,5,5-pentaphenyltrisiloxane; INCI name: trimethyl pentaphenyl trisiloxane). The reference Dow Corning 554 Cosmetic Fluid may also be used.

the phenyl silicone oils corresponding to the following formula:

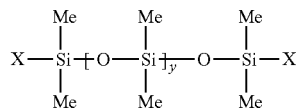

(IV)

in which Me represents methyl, y is between 1 and 1000 and X represents $—CH_2—CH(CH_3)(Ph)$.

the phenyl silicone oils corresponding to formula (V) below:

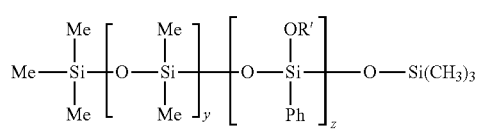

(V)

in which Me is methyl and Ph is phenyl, OR' represents a group $—OSiMe_3$ and y is 0 or ranges between 1 and 1000, and z ranges between 1 and 1000, such that compound (V) is a non-volatile oil.

According to a first embodiment, y ranges between 1 and 1000. Use may be made, for example, of trimethyl siloxyphenyl dimethicone, sold especially under the reference Belsil PDM 1000 sold by the company Wacker.

According to a second embodiment, y is equal to 0. Use may be made, for example, of phenyl trimethylsiloxy trisiloxane, sold especially under the reference Dow Corning 556 Cosmetic Grade Fluid, the phenyl silicone oils corresponding to formula (VI) below, and mixtures thereof:

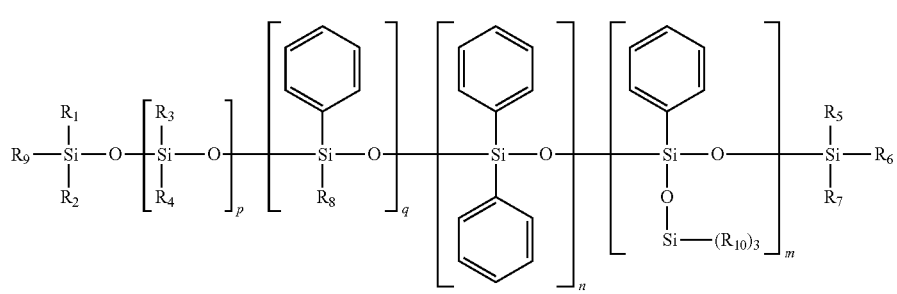

(VI)

in which:

R₁ to R₁₀, independently of each other, are saturated or unsaturated, linear, cyclic or branched $C_1$-$C_{30}$ hydrocarbon-based radicals, m, n, p and q are, independently of each other, integers between 0 and 900, with the proviso that the sum m+n+q is other than 0.

Preferably, the sum m+n+q is between 1 and 100. Preferably, the sum m+n+p+q is between 1 and 900 and better still between 1 and 800. Preferably, q is equal to 0.

the phenyl silicone oils corresponding to formula (VII) below, and mixtures thereof:

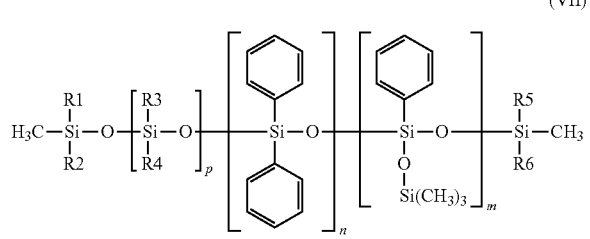

(VII)

in which:

R₁ to R₆, independently of each other, are saturated or unsaturated, linear, cyclic or branched $C_1$-$C_{30}$ hydrocarbon-based radicals, m, n and p are, independently of each other, integers between 0 and 100, with the proviso that the sum n+m is between 1 and 100.

Preferably, R₁ to R₆, independently of each other, represent a saturated, linear or branched $C_1$-$C_{30}$ and especially $C_1$-$C_{12}$ hydrocarbon-based radical and in particular a methyl, ethyl, propyl or butyl radical.

R₁ to R₆ may especially be identical, and in addition may be a methyl radical.

Preferably, m=1 or 2 or 3, and/or n=0 and/or p=0 or 1 may apply, in formula (VII).

the phenyl silicone oils corresponding to formula (VIII) below, and mixtures thereof:

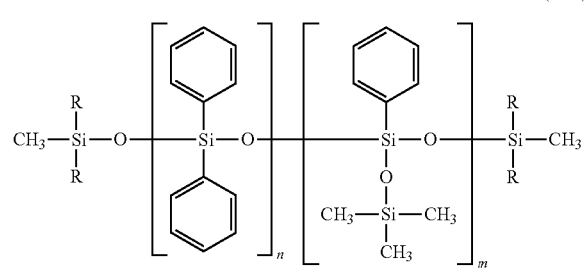

(VIII)

in which:

R is a $C_1$-$C_{30}$ alkyl radical, an aryl radical or an aralkyl radical, n is an integer ranging from 0 to 100, and m is an integer ranging from 0 to 100, with the proviso that the sum n+m ranges from 1 to 100.

In particular, the radicals R of formula (VIII) and R₁ to R₁₀ defined previously may each represent a linear or branched, saturated or unsaturated alkyl radical, especially of $C_2$-$C_{20}$, in particular $C_3$-$C_{16}$ and more particularly $C_4$-$C_{10}$, or a monocyclic or polycyclic $C_6$-$C_{14}$ and especially $C_{10}$-$C_{13}$ aryl radical, or an aralkyl radical whose aryl and alkyl residues are as defined previously.

Preferably, R of formula (VIII) and R₁ to R₁₀ may each represent a methyl, ethyl, propyl, isopropyl, decyl, dodecyl or octadecyl radical, or alternatively a phenyl, tolyl, benzyl or phenethyl radical.

According to one embodiment, a phenyl silicone oil of formula (VIII) with a viscosity at 25° C. of between 5 and 1500 mm²/s (i.e. 5 to 1500 cSt), and preferably with a viscosity of between 5 and 1000 mm²/s (i.e. 5 to 1000 cSt) may be used.

As phenyl silicone oils of formula (VIII), it is especially possible to use phenyl trimethicones such as DC556 from Dow Corning (22.5 cSt), the oil Silbione 70663V30 from Rhône-Poulenc (28 cSt) or diphenyl dimethicones such as Belsil oils, especially Belsil PDM1000 (1000 cSt), Belsil PDM 200 (200 cSt) and Belsil PDM 20 (20 cSt) from Wacker. The values in parentheses represent the viscosities at 25° C.

the phenyl silicone oils corresponding to the following formula, and mixtures thereof:

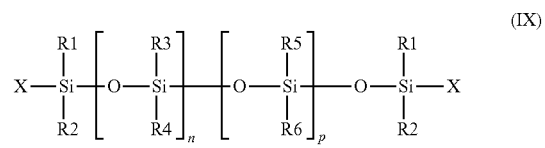

(IX)

in which:

R₁, R₂, R₅ and R₆ are, together or separately, an alkyl radical containing 1 to 6 carbon atoms, R₃ and R₄ are, together or separately, an alkyl radical containing from 1 to 6 carbon atoms or an aryl radical, X is an alkyl radical containing from 1 to 6 carbon atoms, a hydroxyl radical or a vinyl radical, n and p being chosen so as to give the oil a weight-average molecular mass of less than 200 000 g/mol, preferably less than 150 000 g/mol and more preferably less than 100 000 g/mol.

The phenyl silicones that are most particularly suitable for use in the invention are those corresponding to formulae II and V hereinabove.

More particularly, the phenyl silicones are chosen from phenyl trimethicones, phenyl dimethicones, phenyl-trimethylsiloxydiphenylsiloxanes, diphenyl dimethicones, diphenylmethyldiphenyltrisiloxanes and 2-phenylethyl trimethylsiloxysilicates, and mixtures thereof.

Preferably, the weight-average molecular weight of the non-volatile phenyl silicone oil according to the invention ranges from 500 to 10 000 g/mol.

Silicone Gum

According to another embodiment variant, a composition according to the invention contains at least one silicone gum.

The silicone gum that may be used in the invention may be chosen from silicone gums with a viscosity at 25° C. of greater than or equal to 800 000 centistokes (cSt) (800 000× $10^{-6}$ m²/s), especially between 800 000 and 10 000 000 cSt, preferably between 1 000 000 and 500 000 cSt and preferably between 1 000 000 and 2 500 000 cSt. The viscosity of this silicone gum may be measured according to standard ASTM D-445.

The molecular mass of the silicone gums is generally greater than 350 000 g/mol, between 350 000 and 800 000 g/mol and preferably from 450 000 to 700 000 g/mol.

The silicone gum may be chosen especially from the silicones of formula:

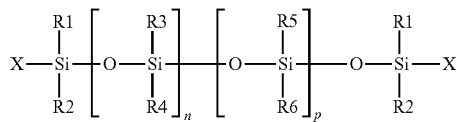

in which:
R$_1$, R$_2$, R$_5$ and R$_6$ are, together or separately, an alkyl radical containing 1 to 6 carbon atoms,
R$_3$ and R$_4$ are, together or separately, an alkyl radical containing from 1 to 6 carbon atoms, a vinyl radical, an amine radical or a hydroxyl radical,
X is an alkyl radical containing from 1 to 6 carbon atoms, a hydroxyl radical or an amine radical,
n and p being integers chosen such that the viscosity of the compound is greater than 800 000 cSt.

As silicone gums that may be used according to the invention, mention may be made of those for which:
  the substituents R$_1$ to R$_6$ represent a methyl group, the group X represents a methyl group, and n and p are such that the molecular weight of the polymer is 600 000 g/mol, such as the product sold under the name Mirasil C-DPDM by the company Bluestar;
  the substituents R$_1$ to R$_6$ represent a methyl group, the group X represents a hydroxyl group, and n and p are such that the molecular weight of the polymer is 600 000 g/mol, such as the product sold under the name SGM 36 by the company Dow Corning:
  dimethicones of the (polydimethylsiloxane)(methylvinylsiloxane) type, such as SE63 sold by GE Bayer Silicones, poly(dimethylsiloxane)(diphenyl)(methylvinylsiloxane) copolymers, and mixtures thereof.

A cosmetic makeup and/or care composition according to the invention also comprises the usual ingredients, as a function of the intended use of the composition.

Solid Fatty Substances

A composition according to the invention may also comprise at least one solid fatty substance especially chosen from waxes and/or pasty fatty substances.

Preferably, the amount of solid fatty substance in the makeup and/or care composition according to the invention is between 0.05% and 50% by weight, especially from 0.1% to 40% by weight or even 0.5% to 30% by weight, relative to the total weight of the composition.

Waxes

According to a first embodiment, the composition is free of wax.

The term "wax" means a lipophilic compound that is solid at room temperature (25° C.), with a reversible solid/liquid change of state, having a melting point of greater than or equal to 30° C., which may be up to 200° C. The waxes may be chosen from waxes of animal, plant, mineral or synthetic origin, and mixtures thereof. Mention may be made especially of hydrocarbon-based waxes, for instance beeswax, lanolin wax and Chinese insect waxes; rice bran wax, carnauba wax, candelilla wax, ouricury wax, alfalfa wax, berry wax, shellac wax, Japan wax and sumach wax; montan wax, orange wax, lemon wax, microcrystalline waxes, paraffins and ozokerite; polyethylene waxes, the waxes obtained by Fisher-Tropsch synthesis and waxy copolymers, and also esters thereof. Mention may also be made of waxes obtained by catalytic hydrogenation of animal or plant oils containing linear or branched C$_8$-C$_{32}$ fatty chains. Among these, mention may be made especially of hydrogenated sunflower oil, hydrogenated castor oil, hydrogenated coconut oil, hydrogenated lanolin oil and bis(1,1,1-trimethylol propane)tetrastearate. Mention may also be made of silicone waxes and fluoro waxes. The waxes obtained by hydrogenation of castor oil esterified with cetyl alcohol may also be used.

Pasty Fatty Substances

According to a first embodiment, the composition is free of pasty fatty substances.

The term "pasty fatty substance" refers to a lipophilic fatty compound with a reversible solid/liquid change of state and comprising, at a temperature of 23° C., a liquid fraction and a solid fraction. The pasty compound preferably has a hardness at 20° C. ranging from 0.001 to 0.5 MPa and preferably from 0.002 to 0.4 MPa. The pasty compound is preferably chosen from synthetic compounds and compounds of plant origin. A pasty compound may be obtained by synthesis from starting materials of plant origin. Mention may be made especially, alone or as a mixture, of:
  lanolin and derivatives thereof, such as lanolin alcohol, oxyethylenated lanolins, acetylated lanolin, lanolin esters such as isopropyl lanolate, and oxypropylenated lanolins,
  polymeric or non-polymeric silicone compounds, for instance polydimethylsiloxanes of high molecular masses, polydimethylsiloxanes containing side chains of the alkyl or alkoxy type containing from 8 to 24 carbon atoms, especially stearyl dimethicones.
  polymeric or non-polymeric fluoro compounds,
  vinyl polymers, especially olefin homopolymers; olefin copolymers; hydrogenated diene homopolymers and copolymers; linear or branched oligomers, homopolymers or copolymers of alkyl(meth)acrylates preferably containing a C$_8$-C$_{30}$ alkyl group; homopolymer and copolymer oligomers of vinyl esters containing C8-C30 alkyl groups; homopolymer and copolymer oligomers of vinyl ethers containing C8-C30 alkyl groups;
  liposoluble polyethers resulting from polyetherification between one or more C$_2$-C$_{100}$ and preferably C$_2$-C$_{50}$ diols; and especially copolymers of ethylene oxide and/or of propylene oxide with long-chain C$_6$-C$_{30}$ alkylene oxides, more preferably such that the weight ratio of the ethylene oxide and/or the propylene oxide to the alkylene oxides in the copolymer is 5/95 to 70/30;
  polyol ethers chosen from polyalkylene glycol pentaerythrityl ethers, fatty alcohol ethers of sugars, and mixtures thereof, polyethylene glycol pentaerythrityl ether comprising five oxyethylene (5 OE) units (CTFA name: PEG-5 pentaerythrityl ether), polypropylene glycol pentaerythrityl ether comprising five oxypropylene (5 OP) units (CTFA name: PPG-5 Pentaerythrityl Ether), and mixtures thereof:
  esters and polyesters; and especially (i) esters of a glycerol oligomer, especially diglycerol esters, in particular condensates of adipic acid and of glycerol, for which some of the hydroxyl groups of the glycerols have reacted with a mixture of fatty acids such as stearic acid, capric acid, stearic acid and isostearic acid and 12-hydroxystearic acid; (ii) phytosterol esters, (iii) pentaerythritol esters; (iv) esters formed from at least one alcohol, at least one of the alcohols being a Guerbet alcohol and from a diacid dimer formed from at least one unsaturated fatty acid; (v) non-crosslinked polyesters resulting from polycondensation between a linear or branched C$_4$-C$_{50}$ dicarboxylic acid or polycarboxylic acid and a C$_2$-C$_{50}$ diol or polyol, (vi) polyesters resulting from the esterification, with a polycarboxylic acid, of an aliphatic hydroxycarboxylic acid ester: (vii) aliphatic esters of an ester resulting from the esterification of an aliphatic hydroxycarboxylic acid ester with an aliphatic carboxylic acid containing especially 4 to 30 carbon atoms. The aliphatic hydroxycarboxylic acid ester is advantageously derived from a hydroxylated aliphatic carboxylic acid containing 2 to 40 carbon atoms and 1 to 20 hydroxyl groups; (viii) aliphatic esters of esters chosen from the ester resulting from the esterification reaction of hydrogenated castor oil with isostearic acid (hydrogenated castor oil mono-, di- or triisostearate).

The pasty compound may also be of plant origin. Mention may be made especially of isomerized jojoba oil, such as trans-isomerized partially hydrogenated jojoba oil; orange wax, shea butter, partially hydrogenated olive oil, cocoa butter and mango oil, Aqueous Phase A composition according to the invention may also comprise an aqueous phase, which may represent 0% to 80% by weight, especially 1% to 70% by weight or even 3% to 60% by weight relative to the total weight of the composition. This aqueous phase may be formed essentially from water, or may comprise a mixture of water and of water-miscible solvent (miscibility in water of greater than 50% by weight at 25° C.) chosen especially from monoalcohols containing 1 to 5 carbon atoms such as ethanol, isopropanol, glycols containing 2 to 8 carbon atoms such as propylene glycol, ethylene glycol, 1,3-butylene glycol, dipropylene glycol, $C_3$-$C_4$ ketones and $C_2$-$C_4$ aldehydes, and mixtures thereof.

However, as stated above, the compositions under consideration according to the invention are advantageously anhydrous or contain less than 3% by weight of water and preferably less than 1% by weight of water relative to the total weight of the composition. The term "anhydrous" especially means that water is preferably not deliberately added to the composition, but may be present in trace amount in the various compounds used in the composition.

Surfactant(s)

A composition according to the invention may also comprise at least one surfactant, which may be present in a proportion of from 0.1% to 10% by weight, especially 0.5% to 8% by weight, or even 1% to 6% by weight relative to the total weight of the composition. The surfactant may be chosen from amphoteric, anionic, cationic and nonionic, preferably nonionic, surfactants. Mention may especially be made, alone or as a mixture, of:

a) nonionic surfactants with an HLB of less than 8 at 25° C., optionally combined with one or more nonionic surfactants with an HLB of greater than 8 at 25° C., as mentioned below, for instance:

saccharide esters and ethers such as sucrose stearates, sucrose cocoate and sorbitan stearate, and mixtures thereof, fatty acid esters, especially of $C_8$-$C_{24}$ and preferably of $C_{16}$-$C_{22}$, and of polyol, especially of glycerol or sorbitol, such as glyceryl stearate, glyceryl laurate, polyglyceryl-2 stearate, sorbitan tristearate and glyceryl ricinoleate;

lecithins, such as soybean lecithins;

oxyethylenated and/or oxypropylenated ethers (which may comprise 1 to 150 oxyethylene and/or oxypropylene groups) of fatty alcohols (especially of $C_8$-$C_{24}$ and preferably $C_{12}$-$C_{18}$ alcohols) such as stearyl alcohol oxyethylene ether containing two oxyethylene units (CTFA name: Steareth-2);

silicone surfactants, for instance dimethicone copolyols and alkyldimethicone copolyols, for example the mixture of cyclomethicone/dimethicone copolyol sold under the name Q2-3225C® by the company Dow Corning b) nonionic surfactants with an HLB of greater than or equal to 8 at 25° C., for instance:

saccharide esters and ethers such as the mixture of cetylstearyl glucoside and of cetyl and stearyl alcohols, for instance Montanov 68 from SEPPIC;

oxyethylenated and/or oxypropylenated glycerol ethers, which may comprise 1 to 150 oxyethylene and/or oxypropylene units;

oxyethylenated and/or oxypropylenated ethers (which may comprise from 1 to 150 oxyethylene and/or oxypropylene units) of fatty alcohols, especially of $C_8$-$C_{24}$ and preferably of $C_{12}$-$C_{18}$, such as stearyl alcohol oxyethylene ether containing 20 oxyethylene units (CTFA name: Steareth-20), cetearyl alcohol oxyethylene ether containing 30 oxyethylene units (Ceteareth-30) and the oxyethylene ether of the mixture of $C_{12}$-$C_{15}$ fatty alcohols comprising 7 oxyethylene units ($C_{12\text{-}15}$ Pareth-7);

esters of a fatty acid, especially of $C_8$-$C_{24}$ and preferably of $C_{16}$-$C_{22}$, and of polyethylene glycol (or PEG) (which may comprise 1 to 150 oxyethylene units), such as PEG-50 stearate and PEG-40 monostearate;

esters of a fatty acid, especially of $C_8$-$C_{24}$ and preferably of $C_{16}$-$C_{22}$, and of oxyethylenated and/or oxypropylenated glycerol ethers (which may comprise from 1 to 150 oxyethylene and/or oxypropylene units), for instance glyceryl monostearate polyoxyethylenated with 200 oxyethylene units; glyceryl stearate polyoxyethylenated with 30 oxyethylene units, glyceryl oleate polyoxyethylenated with 30 oxyethylene units, glyceryl cocoate polyoxyethylenated with 30 oxyethylene units, glyceryl isostearate polyoxyethylenated with 30 oxyethylene units and glyceryl laurate polyoxyethylenated with 30 oxyethylene units;

esters of a fatty acid, especially of $C_8$-$C_{24}$ and preferably of $C_{16}$-$C_{22}$, and of oxyethylenated and/or oxypropylenated sorbitol ethers (which may comprise from 1 to 150 oxyethylene and/or oxypropylene units), for instance polysorbate 20 and polysorbate 60;

dimethicone copolyol, especially the product sold under the name Q2-5220® from Dow Corning;

dimethicone copolyol benzoate, such as the products sold under the names Finsolv SLB 101® and 201® from Finetex;

copolymers of propylene oxide and of ethylene oxide, also known as EO/PO polycondensates, which are copolymers formed from polyethylene glycol and polypropylene glycol blocks, for instance polyethylene glycol/polypropylene glycol/polyethylene glycol triblock polycondensates.

c) anionic surfactants such as:

salts of $C_{16}$-$C_{30}$ fatty acids, especially amine salts, such as triethanolamine stearate or 2-amino-2-methylpropane-1,3-diol stearate;

polyoxyethylenated fatty acid salts, especially animated salts or salts of alkali metals, and mixtures thereof:

phosphoric esters and salts thereof, such as DEA oleth-10 phosphate (Crodafos N 10N from the company Croda) or monopotassium monocetyl phosphate;

sulfosuccinates such as Disodium PEG-5 citrate lauryl sulfosuccinate and Disodium ricinoleamido MEA sulfosuccinate;

alkyl ether sulfates such as sodium lauryl ether sulfate;

isethionates;

acylglutamates such as Disodium hydrogenated tallow glutamate (Amisoft HS21 R® from Ajinomoto) and sodium stearoyl glutamate (Amisoft HS-11 PF® from Ajinomoto);

soybean derivatives, for instance potassium soyate;

citrates, for instance glyceryl stearate citrate;

proline derivatives, for instance sodium palmitoyl proline or the mixture of sodium palmitoyl sarcosinate, magnesium palmitoyl glutamate, palmitic acid and palmitoyl proline (Sepifeel One from SEPPIC);

lactylates, for instance sodium stearoyl lactylate;

sarcosinates, for instance sodium palmitoyl sarcosinate or the 75/25 mixture of stearoyl sarcosine and myristoyl sarcosine;

sulfonates, for instance sodium $C_{14-17}$ alkyl-sec-sulfonate;

glycinates, for instance sodium cocoyl glycinate.

d) cationic surfactants such as:

alkylimidazolidiniums such as isostearylethylimidonium ethosulfate, ammonium salts such as ($C_{12-30}$ alkyl)tri($C_{1-4}$ alkyl)ammonium halides, for instance N,N,N-trimethyl-1-docosanaminium chloride (or Behentrimonium chloride);

e) amphoteric surfactants, for instance N-acylamino acids, such as N-alkylaminoacetates and disodium cocoamphodiacetate, and amine oxides such as stearamine oxide.

Additive(s)

A makeup and/or care composition according to the invention may also comprise at least one agent usually used in cosmetics, chosen, for example, from reducing agents, thickeners, film-forming agents that are especially hydrophobic, silicone elastomers, softeners, anti foams, moisturizers, UV-screening agents, ceramides; cosmetic active agents: peptizers, fragrances, proteins, vitamins, propellants, hydrophilic or lipophilic, film-forming or non-film-forming polymers; lipophilic or hydrophilic gelling agents. The above additives are generally present in an amount for each of them of between 0.01% and 10% by weight relative to the total weight of the composition. Needless to say, a person skilled in the art will take care to select the constituents of the composition such that the advantageous properties associated with the invention are not, or are not substantially, adversely affected.

Thickeners

Thus, a composition according to the invention may also comprise a thickener. The thickener may be chosen from:

organomodified clays, which are clays treated with compounds chosen especially from quaternary amines and tertiary amines. Organomodified clays that may be mentioned include organomodified bentonites, such as the product sold under the name Bentone 34 by the company Rheox, and organomodified hectorites such as the products sold under the names Bentone 27 and Bentone 38 by the company Rheox, hydrophobic fumed silica. Such silicas are sold, for example, under the references Aerosil R812® by the company Degussa and Cab-O-Sil TS-530® by the company Cabot, and under the references Aerosil R972® and Aerosil R974® by the company Degussa and Cab-O—Sil TS-610® and Cab-O—Sil TS-720® by the company Cabot.

The thickener may be present in a content ranging from 0.1% to 5% by weight and better still from 0.4% to 3% by weight relative to the total weight of the composition.

Hydrophobic Film-Forming Polymer

According to one embodiment variant, a composition according to the invention may comprise at least one film-forming polymer, which is in particular hydrophobic.

A cosmetic composition for making up and/or caring for the skin of the lips according to the invention may comprise from 0.1% to 30%, preferably from 0.2% to 20% by weight and even more preferentially from 0.5% to 15% by weight of hydrophobic film-forming polymer(s). This hydrophobic film-forming organic polymer may be a polymer chosen from the group comprising: polyamide silicone block polymers, block ethylenic polymers, vinyl polymers comprising at least one carbosiloxane dendrimer derivative, copolymers comprising carboxylate groups and polydimethylsiloxane groups, silicone resins (T resin, MQ resin) and lipodispersible polymers in the form of a non-aqueous dispersion of polymer particles, and mixtures thereof a) Silicone Resins According to one embodiment variant, a composition according to the invention may comprise, as hydrophobic film-forming polymer, at least one silicone resin.

As silicone resins that may be used in the compositions according to the invention, use may be made, for example, of silicone resins of MQ type, of T type or of MQT type.

MQ Resins:

As examples of silicone resins of MQ type, mention may be made of the alkyl siloxysilicates of formula $[(R1)_3SiO_{1/2}]_x(SiO_{4/2})_y$ (MQ units) in which x and y are integers ranging from 50 to 80, and such that the group R1 represents a radical as defined previously, and is preferably an alkyl group containing from 1 to 8 carbon atoms or a hydroxyl group, preferably a methyl group.

As examples of solid silicone resins of MQ type of trimethyl siloxysilicate type, mention may be made of those sold under the reference SR1000 by the company General Electric, under the reference TMS 803 by the company Wacker, or under the name KF-7312J by the company Shin-Etsu or DC 749 or DC 593 by the company Dow Corning.

As silicone resins comprising MQ siloxysilicate units, mention may also be made of phenylalkylsiloxysilicate resins, such as phenylpropyldimethylsiloxysilicate (Silshine 151 sold by the company General Electric). The preparation of such resins is described especially in U.S. Pat. No. 5,817,302.

T Resins:

Examples of these silicone resins of type T that may be mentioned include the polysilsesquioxanes of formula $(RSiO_{3/2})_x$ (units T) in which x is greater than 100 and such that the group R is an alkyl group containing from 1 to 10 carbon atoms, the said polysilsesquioxanes also possibly comprising Si—OH end groups.

Polymethylsilsesquioxane resins that may preferably be used are those in which R represents a methyl group, for instance those sold:

by the company Wacker under the reference Resin MK, such as Belsil PMS MK: polymer comprising $CH_3SiO_{3/2}$ repeating units (units T), which may also comprise up to 1% by weight of $(CH_3)_2SiO_{2/2}$ units (units D) and having an average molecular weight of about 10 000 g/mol, or by the company Shin-Etsu under the reference KR220L, which are composed of units T of formula $CH_3SiO_{3/2}$ and have Si—OH (silanol) end groups, under the reference KR-242A, which comprise 98% of units T and 2% of dimethyl units D and have Si—OH end groups, or alternatively under the reference KR251 comprising 88% of units T and 12% of dimethyl units D and have Si—OH end groups.

MQT Resins:

Resins comprising MQT units that are especially known are those mentioned in document U.S. Pat. No. 5,110,890.

A preferred form of resins of MQT type are MQT-propyl (also known as MQTpr) resins. Such resins that may be used in the compositions according to the invention are especially the resins described and prepared in patent application WO 2005/075 542, the content of which is incorporated herein by reference.

Preferably, the silicone resin is chosen from the group comprising:

a) a resin of MQ type, chosen especially from (i) alkyl siloxysilicates, which may be trimethyl siloxysilicates, of formula $[(R1)_3SiO_{1/2}]_x(SiO_{4/2})_y$, in which x and y are integers ranging from 50 to 80, and such that the group R1 represents a hydrocarbon-based radical containing from 1 to 10 carbon atoms, a phenyl group, a phenylalkyl group or a hydroxyl group, and preferably is an alkyl group containing from 1 to 8 carbon atoms, preferably a methyl group, and (ii) phenylalkyl siloxysilicate resins, such as phenylpropyldimethyl siloxysilicate, and/or b) a resin of T type, chosen especially from the polysilsesquioxanes of formula $(RSiO_{3/2})_x$, in which x is greater than 100 and the group R is an alkyl group containing from 1 to 10 carbon atoms, for example a methyl group, the said polysilsesquioxanes also possibly comprising Si—OH end groups, and/or c) a resin of MQT type, especially of MQT-propyl type, which may comprise units (i) $(R1_3SiO_{1/2})_a$, (ii) $(R2_2SiO_{2/2})_b$, (iii) $(R3SiO_{3/2})_c$ and (iv) $SiO_{4/2})_d$, with R1, R2 and R3 independently representing a hydrocarbon-based radical, especially alkyl, containing from 1 to 10 carbon atoms, a phenyl group, a phenylalkyl group or a hydroxyl group and preferably an alkyl radical containing from 1 to 8 carbon atoms or a phenyl group, a being between 0.05 and 0.5,
b being between 0 and 0.3,
c being greater than 0,
d being between 0.05 and 0.6,
a+b+c+d=1, and a, b, c and d being mole fractions,
on condition that more than 40 mol % of the groups R3 of the siloxane resin are propyl groups.

b) Lipodispersible Film-Forming Polymers in the Form of Non-Aqueous Dispersions of Polymer particles, also known as NADs According to another embodiment variant, a composition according to the invention may comprise, as hydrophobic film-forming polymer, at least one polymer chosen from lipodispersible film-forming polymers in the form of non-aqueous dispersions of polymer particles, also known as NADs.

Non-aqueous dispersions of hydrophobic film-forming polymer that may be used include dispersions of particles of a grafted ethylenic polymer, preferably an acrylic polymer, in a liquid oily phase:

either in the form of ethylenic polymer particles dispersed in the absence of additional stabilizer at the surface of the particles, as described especially in document WO 04/055 081, or in the form of surface-stabilized particles dispersed in the liquid fatty phase. The dispersion of surface-stabilized polymer particles may be manufactured as described in document EP-A-749 747. The polymer particles may in particular be surface-stabilized by means of a stabilizer that may be a block polymer, a grafted polymer and/or a random polymer, alone or as a mixture. Dispersions of film-forming polymer in the liquid fatty phase, in the presence of stabilizers, are especially described in documents EP-A-748 746, EP-A-923 928 and EP-A-930 060, the content of which is incorporated by reference into the present patent application.

Advantageously, dispersions of ethylenic polymer particles dispersed in the absence of additional stabilizer at the surface of the said particles are used.

Examples of polymers of NAD type that may be mentioned more particularly include acrylic dispersions in isododecane, for instance Mexomer PAP® (acrylic copolymer as a dispersion in isododecane (25%) with pyrene/isoprene copolymer) sold by the company Chimex.

c) Block Ethylenic Copolymer

According to one embodiment of the invention, the film-forming polymer is a block ethylenic copolymer, containing at least a first block with a glass transition temperature (Tg) of greater than or equal to 40° C. and being totally or partly derived from one or more first monomers, which are such that the homopolymer prepared from these monomers has a glass transition temperature of greater than or equal to 40° C., and at least a second block with a glass transition temperature of less than or equal to 20° C. and being derived totally or partly from one or more second monomers, which are such that the homopolymer prepared from these monomers has a glass transition temperature of less than or equal to 20° C., the said first block and the said second block being connected together via a statistical intermediate segment comprising at least one of the said first constituent monomers of the first block and at least one of the said second constituent monomers of the second block, and the said block copolymer having a polydispersity index 1 of greater than 2.

The block polymer used according to the invention thus comprises at least one first block and at least one second block and is prepared exclusively from monofunctional monomers. This means that the block ethylenic polymer used according to the present invention does not contain any multifunctional monomers, which make it possible to break the linearity of a polymer so as to obtain a branched or even crosslinked polymer, as a function of the content of multifunctional monomer. The polymer used according to the invention does not, either, contain any macromonomers (the term "macromonomer" means a monofunctional monomer containing pendent groups of polymeric nature, and preferably having a molecular mass of greater than 500 g/mol, or alternatively a polymer comprising on only one of its ends a polymerizable (or ethylenically unsaturated) end group), which are used in the preparation of a grafted polymer.

The term "block" polymer means a polymer comprising at least two different blocks and preferably at least three different blocks.

The term "ethylenic" polymer means a polymer obtained by polymerization of ethylenically unsaturated monomers.

It is pointed out that, in the text hereinabove and hereinbelow, the terms "first" and "second" blocks do not in any way condition the order of the said blocks in the structure of the block polymer.

The first block and the second block of the polymer used in the invention may be advantageously mutually incompatible.

The term "mutually incompatible blocks" means that the mixture formed from the polymer corresponding to the first block and form the polymer corresponding to the second block is not miscible in the polymerization solvent that is in major amount by weight for the block polymer, at room temperature (25° C.) and atmospheric pressure ($10^5$ Pa), for a content of the mixture of the said polymers of greater than or equal to 5% by weight, relative to the total weight of the mixture of the said polymers and of the said polymerization solvent, it being understood that:

i) the said polymers are present in the mixture in a content such that the respective weight ratio ranges from 10/90 to 90/10, and that ii) each of the polymers corresponding to the first and second blocks has an average (weight-average or number-average) molecular mass equal to that of the block polymer ±15%.

In the case of a mixture of polymerization solvents, and in the event that two or more solvents are present in identical mass proportions, the said polymer mixture is immiscible in at least one of them. Needless to say, in the case of a polymerization performed in a single solvent, this solvent is the solvent that is in major amount.

The block polymer according to the invention comprises at least a first block and at least a second block that are connected together via an intermediate segment comprising at least one constituent monomer of the first block and at least one constituent monomer of the second block. The intermediate segment (also known as the intermediate block) has a glass transition temperature Tg that is between the glass transition temperatures of the first and second blocks.

The intermediate segment is a block comprising at least one constituent monomer of the first block and at least one constituent monomer of the second block of the polymer allowing these blocks to be "compatibilized".

Advantageously, the intermediate segment comprising at least one constituent monomer of the first block and at least one constituent monomer of the second block of the block polymer is a statistical polymer.

Preferably, the intermediate block is derived essentially from constituent monomers of the first block and of the second block.

The term "essentially" means at least 85%, preferably at least 90%, better still 95% and even better still 100%.

The block polymer according to the invention is advantageously a film-forming block ethylenic polymer. The term "ethylenic" polymer means a polymer obtained by polymerization of ethylenically unsaturated monomers. The term "film-forming polymer" means a polymer that is capable of forming, by itself or in the presence of an auxiliary film-forming agent, a continuous deposit on a support, especially on keratin materials.

Preferentially, the polymer according to the invention does not comprise any silicon atoms in its backbone. The term "backbone" means the main chain of the polymer, as opposed to the pendent side chains.

Preferably, the polymer according to the invention is not water-soluble, i.e. the polymer is not soluble in water or in a mixture of water and linear or branched lower monoalcohols containing from 2 to 5 carbon atoms, for instance ethanol, isopropanol or n-propanol, without modifying the pH, at the solids content of at least 1% by weight, at room temperature (25° C.).

Preferably, the polymer according to the invention is not an elastomer.

The polydispersity index of the polymer of the invention is greater than 2, for example ranging from 2 to 9. Preferably, it is greater than or equal to 2.5, for example ranging from 2.5 to 8, and better still greater than or equal to 2.8 and especially ranging from 2.8 to 6.

The polydispersity index I of the polymer is equal to the ratio of the weight-average molecular mass Mw to the number-average molecular mass Mn.

The weight-average molar mass (Mw) and number-average molar mass (Mn) are determined by gel permeation liquid chromatography (THF solvent, calibration curve established with linear polystyrene standards, refractometric detector).

The weight-average mass (Mw) of the polymer according to the invention is preferably less than or equal to 300 000; it ranges, for example, from 35 000 to 200 000 and better still from 45 000 to 150 000 g/mol.

The number-average mass (Mn) of the polymer according to the invention is preferably less than or equal to 70 000: it ranges, for example, from 10 000 to 60 000 and better still from 12 000 to 50 000 g/mol.

First Block with a Tg of Greater than or Equal to 40° C.,

The block with a Tg of greater than or equal to 40° C. has, for example, a Tg ranging from 40 to 150° C., preferably greater than or equal to 50° C., for example ranging from 50° C. to 120° C. and better still greater than or equal to 60° C., for example ranging from 60° C. to 120° C.

The glass transition temperatures indicated for the first and second blocks may be theoretical Tg values determined from the theoretical Tg values of the constituent monomers of each of the blocks, which may be found in a reference manual such as the Polymer Handbook, 3rd Edition, 1989, John Wiley.

The block with a Tg of greater than or equal to 40° C. may be a homopolymer or a copolymer.

The block with a Tg of greater than or equal to 40° C. may be derived totally or partially from one or more monomers which are such that the homopolymer prepared from these monomers has a glass transition temperature of greater than or equal to 40° C. This block may also be referred to as a "rigid block".

When this block is a homopolymer, it is derived from only one type of monomer for which the Tg of the corresponding homopolymer is greater than or equal to 40° C.

In the case where the first block is a copolymer, it may be totally or partially derived from one or more monomers, the nature and concentration of which are chosen such that the Tg of the resulting copolymer is greater than or equal to 40° C. The copolymer may comprise, for example:

monomers which are such that the homopolymers prepared from these monomers have Tg values of greater than or equal to 40° C., for example a Tg ranging from 40 to 150° C., preferably greater than or equal to 50° C., for example ranging from 50° C. to 120° C. and better still greater than or equal to 60° C., for example ranging from 60° C. to 120° C., and monomers which are such that the homopolymers prepared from these monomers have Tg values of less than 40° C., chosen from monomers with a Tg of between 20 and 40° C. and/or monomers with a Tg of less than or equal to 20° C., for example a Tg ranging from −100 to 20° C., preferably less than 15° C., especially ranging from −80° C. to 15° C. and better still less than 10° C., for example ranging from −50° C. to 0° C., as described later. The monomers and the proportions thereof are preferably chosen such that the glass transition temperature of the first block is greater than or equal to 40° C.

The first monomers whose homopolymers have a glass transition temperature of greater than or equal to 40° C. are chosen, preferably, from the following monomers, also known as the main monomers:

the methacrylates of formula $CH_2=C(CH_3)-COOR_1$ in which $R_1$ represents a linear or branched unsubstituted alkyl group containing from 1 to 4 carbon atoms, such as a methyl, ethyl, propyl or isobutyl group or $R_1$ represents a $C_4$ to $C_{12}$ cycloalkyl group, preferably a $C_8$ to $C_{12}$ cycloalkyl, such as isobornyl methacrylate, the acrylates of formula $CH_2=CH-COOR_2$ in which $R_2$ represents a $C_4$ to $C_{12}$ cycloalkyl group such as an isobornyl group or a tert-butyl group, the (meth)acrylamides of formula:

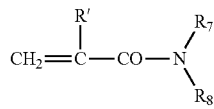

in which $R_7$ and $R_8$, which may be identical or different, each represent a hydrogen atom or a linear or branched $C_1$ to $C_{12}$ alkyl group such as an n-butyl, t-butyl, isopropyl, isohexyl, isooctyl or isononyl group; or $R_7$ represents H and $R_8$ represents a 1,1-dimethyl-3-oxobutyl group, and R' denotes H or methyl. Examples of monomers that may be mentioned include N-butylacrylamide, N-tert-butylacrylamide, N-isopropylacrylamide, N,N-dimethylacrylamide and N,N-dibutylacrylamide, and mixtures thereof.

According to one embodiment, the first block is obtained from:

i) at least one acrylate monomer of formula $CH_2$=CH—$COOR_2$ in which $R_2$ represents a $C_4$ to $C_{12}$ cycloalkyl group, preferably a $C_8$ to $C_{12}$ cycloalkyl, such as isobornyl, ii) and at least one methacrylate monomer of formula $CH_2$=$C(CH_3)$—$COOR'_2$ in which $R'_2$ represents a $C_4$ to $C_{12}$ cycloalkyl group, preferably a $C_8$ to $C_{12}$ cycloalkyl, such as isobornyl.

Preferably, $R_2$ and $R'_2$ represents, independently or simultaneously, an isobornyl group.

The first block may be obtained exclusively from the said acrylate monomer and from the said methacrylate monomer. Preferably, these monomers are in mass proportions of between 30/70 and 70/30, preferably between 40/60 and 60/40, especially about 50/50.

The proportion of the first block advantageously ranges from 20% to 90%, better still from 30% to 80% and even better still from 60% to 80% by weight of the polymer.

According to one embodiment, the first block is obtained by polymerization of isobornyl methacrylate and isobornyl acrylate.

Second Block with a Glass Transition Temperature of Less than 20° C.

The second block advantageously has a glass transition temperature Tg of less than or equal to 20° C., for example, a Tg ranging from −100 to 20° C., preferably less than or equal to 15° C., especially ranging from −80° C. to 15° C. and better still less than or equal to 10° C., for example ranging from −100° C. to 10° C., especially ranging from −30° C. to 10° C.

The second block is totally or partially derived from one or more second monomers, which are such that the homopolymer prepared from these monomers has a glass transition temperature of less than or equal to 20° C.

The monomer with a Tg of less than or equal to 20° C. (known as the second monomer) is preferably chosen from the following monomers:

the acrylates of formula $CH_2$=CH—$COOR_3$ $R_3$ representing a linear or branched $C_1$ to $C_{12}$ unsubstituted alkyl group, with the exception of the tert-butyl group, in which one or more heteroatoms chosen from O, N and S are optionally intercalated, the methacrylates of formula $CH_2$=$C(CH_3)$—$COOR_4$ $R_4$ representing a linear or branched $C_6$ to $C_{12}$ unsubstituted alkyl group, in which one or more heteroatoms chosen from O, N and S is (are) optionally intercalated;

the vinyl esters of formula $R_5$—CO—O—CH=$CH_2$ in which $R_5$ represents a linear or branched $C_4$ to $C_{12}$ alkyl group;

ethers of vinyl alcohol and of a $C_4$ to $C_{12}$ alcohol,

N—($C_4$ to $C_{12}$)alkyl acrylamides, such as N-octylacrylamide, and mixtures thereof.

The preferred monomers with a Tg of less than or equal to 20° C. are isobutyl acrylate, 2-ethylhexyl acrylate or mixtures thereof in all proportions.

Each of the first and second blocks may contain in small proportion at least one constituent monomer of the other block.

Each of the first and/or second blocks may comprise, in addition to the monomers indicated above, one or more other monomers known as additional monomers, which are different from the main monomers mentioned above.

The nature and amount of this or these additional monomer(s) are chosen such that the block in which they are present has the desired glass transition temperature.

This additional monomer is chosen, for example, from (meth)acrylic acid, preferably acrylic acid, and mixtures thereof.

The additional monomer may represent 0.5% to 30% by weight relative to the weight of the polymer. According to one embodiment, the polymer of the invention does not contain any additional monomer.

According to one embodiment, the first block does not comprise any additional monomer.

According to a preferred embodiment, the second block comprises acrylic acid as additional monomer.

Preferably, the polymer of the invention comprises at least isobornyl acrylate and isobornyl methacrylate monomers in the first block and isobutyl acrylate and acrylic acid monomers in the second block.

Preferably, the polymer comprises at least isobornyl acrylate and isobornyl methacrylate monomers in equivalent weight proportion in the first block and isobutyl acrylate and acrylic acid monomers in the second block. Advantageously, the first block represents 70% by weight of the polymer Preferably, the acrylic acid represents 5% by weight of the polymer.

The block copolymer may advantageously comprise more than 2% by weight of acrylic acid monomers, and especially from 2% to 15% by weight, for example from 3% to 15% by weight, in particular from 4% to 15% by weight or even from 4% to 10% by weight of acrylic acid monomers, relative to the total weight of the said copolymer.

Preferably, the block copolymer comprises from 50% to 80% by weight of isobornyl methacrylate/acrylate, from 10% to 30% by weight of isobutyl acrylate and from 2% to 10% by weight of acrylic acid.

Intermediate Segment

The intermediate segment (also known as the intermediate block) connects the first block and the second block of the polymer used according to the present invention. The intermediate segment results from the polymerization:

i) of the first monomer(s), and optionally of the additional monomer(s), which remain available after their polymerization to a maximum degree of conversion of 90% to form the first block, ii) and of the second monomer(s), and optionally of the additional monomer(s), added to the reaction mixture.

The formation of the second block is initiated when the first monomers no longer react or are no longer incorporated into the polymer chain either because they are all consumed or because their reactivity no longer allows them to be.

Thus, the intermediate segment comprises the first available monomers, resulting from a degree of conversion of these first monomers of less than or equal to 90%, during the introduction of the second monomer(s) during the synthesis of the polymer.

The intermediate segment of the block polymer is a statistical polymer (which may also be referred to as a statistical block). This means that it comprises a statistical distribution of the first monomer(s) and of the second monomer(s) and also of the additional monomer(s) that may be present.

Thus, the intermediate segment is a statistical block, as are the first block and the second block if they are not homopolymers (i.e. if they are both formed from at least two different monomers).

Process for Preparing the Copolymer

The block ethylenic copolymer according to the invention is prepared by free radical polymerization, according to the techniques that are well known for this type of polymerization. In particular, it may be prepared according to the process described in patent application FR 0 953 625, the content of which is incorporated herein by reference.

Preferably, the block ethylenic copolymer is present in the composition in an active material content ranging from 0.1% to 60%, better still from 0.5% to 50%, better still from 1% to 30% and even better still from 1% to 40% by weight relative to the total weight of the composition.

Distillation of the Synthesis Solvent

It is possible to perform a step of total or partial removal of the said volatile oil or solvent (conventionally isododecane). This is then performed in particular by distillation, optionally under vacuum, and optional addition of non-volatile hydrocarbon-based ester oil comprising at least 16 carbon atoms and having a molar mass of less than 650 g/mol, such as octyldodecyl neopentanoate (especially 2-octyldodecyl neopentanoate).

This step is performed at elevated temperature and optionally under vacuum to distil off a maximum amount of volatile synthesis solvent, and is known to those skilled in the art.

d) Polyamide Silicone Block Polymer

According to another embodiment variant, a composition according to the invention comprises, as hydrophobic film-forming polymer, at least one polyamide silicone block polymer, also known as a silicone polyamide.

The silicone polyamides are preferably solid at room temperature (25° C.) and atmospheric pressure (760 mmHg).

For the purposes of the invention, the term "polymer" means a compound containing at least two repeating units, preferably at least three repeating units and better still ten repeating units.

The silicone polyamides of the composition of the invention may be polymers of the polyorganosiloxane type, for instance those described in documents U.S. Pat. Nos. 5,874, 069, 5,919,441, 6,051,216 and 5,981,680. According to the invention, the silicone polymers may belong to the following two families:

(1) polyorganosiloxanes comprising at least two amide groups, these two groups being located in the polymer chain, and/or (2) polyorganosiloxanes comprising at least two amide groups, these two groups being located on grafts or branches.

According to one variant of the invention, a polymer may also be used comprising at least one unit of formula (III) or (IV):

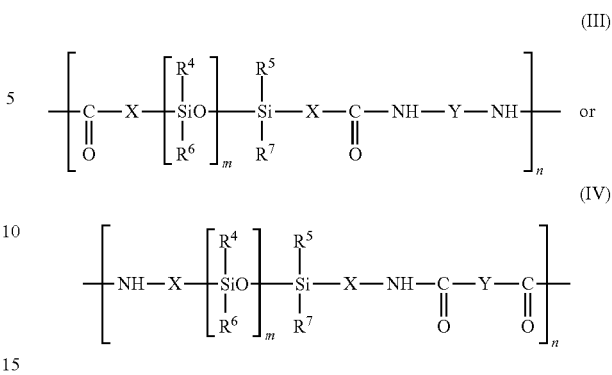

in which:
1) $R^4$, $R^5$, $R^6$ and $R^7$ which may be identical or different, represent a group chosen from:
 linear, branched or cyclic, saturated or unsaturated, $C_1$ to $C_{40}$ hydrocarbon-based groups, possibly containing in their chain one or more oxygen, sulfur and/or nitrogen atoms, and possibly being partially or totally substituted with fluorine atoms,
 $C_6$-$C_{10}$ aryl groups, optionally substituted with one or more $C_1$-$C_4$ alkyl groups,
 polyorganosiloxane chains possibly containing one or more oxygen, sulfur and/or nitrogen atoms,
2) the groups X, which may be identical or different, represent a linear or branched $C_1$-$C_{30}$ alkylenediyl group, possibly containing in its chain one or more oxygen and/or nitrogen atoms;
3) Y is a saturated or unsaturated $C_1$ to $C_{50}$ linear or branched alkylene, arylene, cycloalkylene, alkylarylene or arylalkylene divalent group, which may comprise one or more oxygen, sulfur and/or nitrogen atoms, and/or may bear as substituent one of the following atoms or groups of atoms: fluorine, hydroxyl, $C_3$ to $C_8$ cycloalkyl, $C_1$ to $C_{40}$ alkyl, $C_5$ to $C_{10}$ aryl, phenyl optionally substituted with 1 to 3 $C_1$ to $C_3$ alkyl, $C_1$ to $C_3$ hydroxyalkyl and $C_1$ to $C_6$ aminoalkyl groups, or
4) Y represents a group corresponding to the formula:

in which:
T represents a linear or branched, saturated or unsaturated, $C_3$-$C_{24}$ trivalent or tetravalent hydrocarbon-based group optionally substituted with a polyorganosiloxane chain, and possibly containing one or more atoms chosen from O, N and S, or T represents a trivalent atom chosen from N, P and Al, and
$R^8$ represents a linear or branched $C_1$-$C_{50}$ alkyl group or a polyorganosiloxane chain, possibly comprising one or more ester, amide, urethane, thiocarbamate, urea, thiourea and/or sulfonamide groups, which may possibly be linked to another chain of the polymer; and
5) n is an integer ranging from 2 to 500 and preferably from 2 to 200, and m is an integer ranging from 1 to 1000, preferably from 1 to 700 and better still from 6 to 200.

According to the invention, 80% of the groups $R^4$, $R^5$, $R^6$ and $R^7$ of the polymer are preferably chosen from methyl, ethyl, phenyl and 3,3,3-trifluoropropyl groups.

According to the invention, Y can represent various divalent groups, furthermore optionally comprising one or two free valencies to establish bonds with other moieties of the polymer or copolymer. Preferably, Y represents a group chosen from:

a) linear $C_1$ to $C_{20}$ and preferably $C_1$ to $C_{10}$ alkylene groups, b) branched $C_{30}$ to $C_{56}$ alkylene groups possibly comprising rings and unconjugated unsaturations, c) $C_5$-$C_6$ cycloalkylene groups, d) phenylene groups optionally substituted with one or more $C_1$ to $C_{40}$ alkyl groups, e) $C_1$ to $C_{20}$ alkylene groups comprising from 1 to 5 amide groups, f) $C_1$ to $C_{20}$ alkylene groups comprising one or more substituents chosen from hydroxyl, $C_3$ to $C_8$ cycloalkane, $C_1$ to $C_3$ hydroxyalkyl and $C_1$ to $C_6$ alkylamine groups, g) polyorganosiloxane chains of formula:

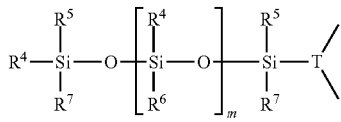

in which $R^4$, $R^5$, $R^6$, $R^7$, T and m are as defined above, and h) polyorganosiloxane chains of formula:

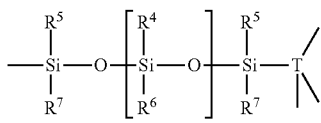

In these polyamides of formula (III) or (IV), m ranges from 1 to 700, in particular from 15 to 500 and especially from 50 to 200, and n ranges in particular from 1 to 500, preferably from 1 to 100 and better still from 4 to 25, X is preferably a linear or branched alkylene chain containing from 1 to 30 carbon atoms, in particular 1 to 20 carbon atoms, especially from 5 to 15 carbon atoms and more particularly 10 carbon atoms, and Y is preferably an alkylene chain that is linear or branched, or which may comprise rings and/or unsaturations, containing from 1 to 40 carbon atoms, in particular 1 to 20 carbon atoms and better still from 2 to 6 carbon atoms, in particular 6 carbon atoms.

In formulae (III) and (IV), the alkylene group representing X or Y can optionally contain in its alkylene part at least one of the following components:

1) one to five amide, urea, urethane or carbamate groups, 2) a $C_5$ or $C_6$ cycloalkyl group, and 3) a phenylene group optionally substituted with 1 to 3 identical or different $C_1$-$C_3$ alkyl groups.

In formulae (III) and (IV), the alkylene groups may also be substituted with at least one component chosen from the group consisting of:
a hydroxyl group,
a $C_3$ to $C_8$ cycloalkyl group,
one to three $C_1$ to $C_{40}$ alkyl groups,
a phenyl group optionally substituted with one to three $C_1$ to $C_3$ alkyl groups,
a $C_1$ to $C_3$ hydroxyalkyl group, and
a $C_1$ to $C_6$ aminoalkyl group.

In these formulae (III) and (IV), Y may also represent:

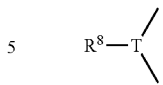

in which $R^8$ represents a polyorganosiloxane chain and T represents a group of formula:

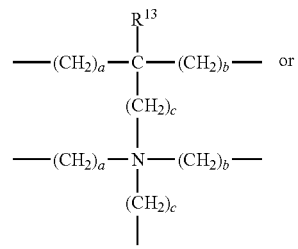

in which a, b and c are, independently, integers ranging from 1 to 10, and $R^{13}$ is a hydrogen atom or a group such as those defined for $R^4$, $R^5$, $R^6$ and $R^7$.

In formulae (III) and (IV), $R^4$, $R^5$, $R^6$ and $R^7$ preferably represent, independently, a linear or branched $C_1$ to $C_{40}$ alkyl group, preferably a $CH_3$, $C_2H_5$, $nC_3H_7$ or isopropyl group, a polyorganosiloxane chain or a phenyl group optionally substituted with one to three methyl or ethyl groups.

As has been seen previously, the polymer may comprise identical or different units of formula (III) or (IV).

Advantageously, the composition according to the invention comprises at least one polydimethylsiloxane block polymer of general formulae (II) and (IV) with an index m of about 15.

More preferably, the composition according to the invention comprises at least one polymer comprising at least one unit of formula (III) in which m ranges from 5 to 100, in particular from 10 to 75 and even more particularly is about 15; even more preferably, $R^4$, $R^5$, $R^6$ and $R^7$ independently represent a linear or branched $C_1$ to $C_{40}$ alkyl group, preferably a group $CH_3$, $C_2H_5$, $nC_3H_7$ or isopropyl in formula (III).

As examples of silicone polymers that may be used, mention may be made of one of the silicone polyamides obtained in accordance with Examples 1 to 3 of document U.S. Pat. No. 5,981,680.

According to one particularly preferred embodiment, the composition according to the invention comprises at least one polydimethylsiloxane block polymer of general formulae (III) and (IV) with an index m of about 100.

More preferably, the composition according to the invention comprises at least one polymer comprising at least one unit of formula (III) in which m ranges from 50 to 200, in particular from 75 to 150 and even more particularly is about 100; even more preferably, $R^4$, $R^5$, $R^6$ and $R^7$ independently represent a linear or branched $C_1$ to $C_{40}$ alkyl group, preferably a group $CH_3$, $C_2H_5$, $nC_3H_7$ or isopropyl in formula (III).

As examples of silicone polymers that may preferably be used according to this embodiment, mention may be made of the silicone polyamides sold by the company Dow Corning under the name DC 2-8179 (DP 100).

According to one preferred embodiment, the silicone polyamide comprises units of formula III, preferably in which the groups R4, R5, R6 and R7 represent methyl groups, one from among X and Y represents an alkylene group of 6 carbon atoms and the other represents an alkylene group of 11 carbon atoms, n representing the degree of polymerization, DP, of the polymer.

By way of example of such silicone polyamides, mention may be made of the compounds sold by the company Dow Corning under the names DC 2-8179 (DP 100) and DC 2-8178 (DP 15), the INCI name of which is Nylon-611/dimethicone copolymer. Preferably, the silicone polyamide sold by the company Dow Corning under the name DC 2-8179 (DP 100) will be used.

e) Vinyl Polymer Comprising at Least One Carbosiloxane Dendrimer-Based Unit

According to one particular embodiment, a composition used according to the invention may comprise, as hydrophobic film-forming polymer, at least one vinyl polymer comprising at least one carbosiloxane dendrimer-based unit.

The vinyl polymer may especially have a backbone and at least one side chain, which comprises a carbosiloxane dendrimer structure.

The term "carbosiloxane dendrimer structure" in the context of the present invention represents a structure with branched groups of high molecular masses with high regularity in the radial direction starting from the bond to the backbone. Such carbosiloxane dendrimer structures are described in the form of a highly branched siloxane-silylalkylene copolymer in the laid-open Japanese patent application Kokai 9-171 154.

According to one preferred mode, the vinyl polymer grafted with a carbosiloxane dendrimer used comprises at least one butyl acrylate monomer.

According to one embodiment, the vinyl polymer also comprises at least one fluoro organic group.

The vinyl polymers represented by the formulae presented below are preferable:

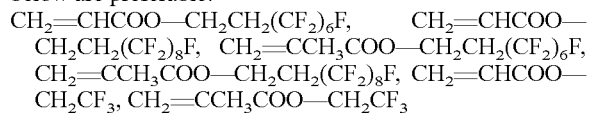

The vinyl polymers represented by the formulae presented below are particularly preferable:

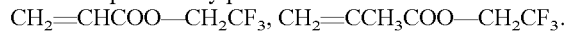

According to one preferred embodiment, vinyl polymers grafted within the meaning of the present invention are conveyed in an oil, which is preferably volatile, chosen from silicone oils and/or hydrocarbon-based oils.

According to one particular embodiment, the silicone oil may be cyclopentasiloxane.

According to another particular embodiment, a hydrocarbon-based oil may be isododecane.

Vinyl polymers grafted with at least one carbosiloxane dendrimer-based unit that may be particularly suitable for use in the present invention are the polymers sold under the names TIB 4-100, TIB 4-101, TIB 4-120, TIB 4-130, TIB 4-200, FA 4002 ID (TIB 4-202), TIB 4-220 and FA 4001 CM (TIB 4-230) by the company Dow Corning.

Preferably, the vinyl polymer grafted with at least one carbosiloxane dendrimer-based unit that may be used in a composition of the invention is an acrylate/polytrimethyl siloxymethacrylate copolymer, especially the product sold in isododecane under the name Dow Corning FA 4002 ID Silicone Acrylate by the company Dow Corning.

f) Copolymers Comprising Carboxylate Groups and Polydimethylsiloxane Groups

In the present patent application, the expression "copolymer comprising carboxylate groups and polydimethylsiloxane groups" means a copolymer obtained from (a) one or more carboxylic (acid or ester) monomers, and (b) one or more polydimethylsiloxane (PDMS) chains.

In the present patent application, the term "carboxylic monomer" means both carboxylic acid monomers and carboxylic acid ester monomers. Thus, the monomer (a) may be chosen, for example, from acrylic acid, methacrylic acid, maleic acid, fumaric acid, itaconic acid, crotonic acid, esters thereof and mixtures of these monomers. Esters that may be mentioned include the following monomers: acrylate, methacrylate, maleate, fumarate, itaconate and/or crotonate. According to one preferred embodiment of the invention, the monomers in ester form are more particularly chosen from linear or branched, preferably $C_1$-$C_{24}$ and better still $C_1$-$C_{22}$ alkyl acrylates and methacrylates, the alkyl radical preferably being chosen from methyl, ethyl, stearyl, butyl and 2-ethylhexyl radicals, and mixtures thereof.

Thus, according to one particular embodiment of the invention, the copolymer comprises as carboxylate groups at least one group chosen from acrylic acid and methacrylic acid, and methyl, ethyl, stearyl, butyl or 2-ethylhexyl acrylate or methacrylate, and mixtures thereof.

In the present patent application, the term "polydimethylsiloxanes" (also known as organopolysiloxanes and abbreviated as PDMS) denotes, in accordance with what is generally accepted, any organosilicon polymer or oligomer of linear structure, of variable molecular weight, obtained by polymerization and/or polycondensation of suitably functionalized silanes, and consisting essentially of a repetition of main units in which the silicon atoms are linked together via oxygen atoms (siloxane bond ≡Si—O—Si≡), comprising trimethyl radicals directly linked via a carbon atom to the said silicon atoms. The PDMS chains that may be used to obtain the copolymer used according to the invention comprise at least one polymerizable radical group, preferably located on at least one of the ends of the chain, i.e. the PDMS may contain, for example, a polymerizable radical group on the two ends of the chain or one polymerizable radical group on one end of the chain and one trimethylsilyl end group on the other end of the chain. The radical-polymerizable group may especially be an acrylic or methacrylic group, in particular a group $CH_2$=$CR_1$—CO—O—$R_2$, in which $R_1$ represents a hydrogen or a methyl group, and $R_2$ represents —$CH_2$—, —$(CH_2)_n$— with n=3, 5, 8 or 10, —$CH_2$—$CH(CH_3)$—$CH_2$—, —$CH_2$—$CH_2$—O—$CH_2$—$CH_2$—, —$CH_2$—$CH_2$—O—$CH_2$—$CH_2$—$CH(CH_3)$—$CH_2$— or —$CH_2$—$CH_2$—O—$CH_2$, $CH_2$—O—$CH_2$—$CH_2$—$CH_2$—.

The copolymers used in the composition of the invention are generally obtained according to the usual methods of polymerization and grafting, for example by free-radical polymerization (A) of a PDMS comprising at least one polymerizable radical group (for example on one of the ends of the chain or on both ends) and (B) of at least one carboxylic monomer, as described, for example, in documents U.S. Pat. Nos. 5,061,481 and 5,219,560.

The copolymers obtained generally have a molecular weight ranging from about 3000 to 200 000 and preferably from about 5000 to 100 000.

The copolymer used in the composition of the invention may be in its native form or in dispersed form in a solvent such as lower alcohols containing from 2 to 8 carbon atoms, for instance isopropyl alcohol, or oils, for instance volatile silicone oils (for example cyclopentasiloxane).

As copolymers that may be used in the composition of the invention, mention may be made, for example, of copolymers of acrylic acid and of stearyl acrylate containing polydimethylsiloxane grafts, copolymers of stearyl methacrylate containing polydimethylsiloxane grafts, copolymers of acrylic acid and of stearyl methacrylate containing polydimethylsiloxane grafts, copolymers of methyl methacrylate, butyl methacrylate, 2-ethylhexyl acrylate and stearyl methacrylate containing polydimethylsiloxane grafts. As copolymers that may be used in the composition of the invention, mention may be made in particular of the copolymers sold by the company Shin-Etsu under the names KP-561 (CTFA name: acrylates/dimethicone), KP-541 in which the copolymer is dispersed at 60% by weight in isopropyl alcohol (CTFA name: acrylates/dimethicone and isopropyl alcohol), and KP-545 in which the copolymer is dispersed at 30% in cyclopentasiloxane (CTFA name: acrylates/dimethicone and cyclopentasiloxane). According to one preferred embodiment of the invention, KP561 is preferably used; this copolymer is not dispersed in a solvent, but is in waxy form, its melting point being about 30° C.

Mention may also be made of the grafted copolymer of polyacrylic acid and dimethylpolysiloxane dissolved in isododecane, sold by the company Shin-Etsu under the name KP-550.

Silicone Elastomer

According to another embodiment variant, a composition according to the invention may comprise at least one silicone elastomer, also known as an organopolysiloxane elastomer.

The term "organopolysiloxane elastomer" means a deformable, flexible organopolysiloxane with viscoelastic properties and especially the consistency of a sponge or of a supple sphere. Its modulus of elasticity is such that this material withstands deformation and has limited stretchability and contractability. This material is capable of regaining its original shape after stretching.

It is more particularly a crosslinked organopolysiloxane elastomer.

Preferably, the organopolysiloxane elastomer is obtained by crosslinking addition reaction (A) of diorganopolysiloxane containing at least two hydrogens each bonded to a silicon, and (B) of diorganopolysiloxane containing at least two ethylenically unsaturated groups bonded to silicon, especially in the presence (C) of a platinum catalyst, as described, for instance, in patent application EP-A-295 886.

In particular, the organopolysiloxane elastomer may be obtained by reaction of a dimethylpolysiloxane with dimethylvinylsiloxy end groups and of methylhydrogenopolysiloxane with trimethylsiloxy end groups, in the presence of a platinum catalyst.

Compound (A) may especially be chosen from methylhydrogenopolysiloxanes containing trimethylsiloxy end groups, dimethylsiloxane-methylhydrogenosiloxane copolymers containing trimethylsiloxy end groups, dimethylsiloxane-methylhydrogenosiloxane cyclic copolymers.

The organopolysiloxanes (B) may be chosen in particular from methylvinylpolysiloxanes, methylvinylsiloxane-dimethylsiloxane copolymers, dimethylpolysiloxanes containing dimethylvinylsiloxy end groups, dimethylsiloxane-methylphenylsiloxane copolymers containing dimethylvinylsiloxy end groups, dimethylsiloxane-diphenylsiloxane-methylvinyl siloxane copolymers containing dimethylvinylsiloxy end groups, dimethylsiloxane-methylvinylsiloxane copolymers containing trimethylsiloxy end groups, dimethylsiloxane-methylphenylsiloxane-methylvinylsiloxane copolymers containing trimethylsiloxy end groups, methyl(3,3,3-trifluoropropyl)polysiloxanes containing dimethyl vinyl siloxy end groups, and dimethylsiloxane-methyl(3,3,3-trifluoropropyl)siloxane copolymers containing dimethylvinylsiloxy end groups.

It is advantageous for compound (A) to be added in an amount such that the molecular ratio between the total amount of hydrogen atoms bonded to silicon atoms in compound (A) and the total amount of all the ethyleni-cally unsaturated groups in compound (B) is within the range from 1.5/1 to 20/1.

Compound (C) is the catalyst for the crosslinking reaction, and is especially chloroplatinic acid, chloroplatinic acid-olefin complexes, chloroplatinic acid-alkenylsiloxane complexes, chloroplatinic acid-diketone complexes, platinum black and platinum on a support.

The catalyst (C) is preferably added in an amount of from 0.1 to 1000 parts by weight and better still from 1 to 100 parts by weight, as clean platinum metal, per 1000 parts by weight of the total amount of compounds (A) and (B).

The elastomer is advantageously a non-emulsifying elastomer.

The term "non-emulsifying" defines organopolysiloxane elastomers not containing a hydrophilic chain, and in particular not containing any polyoxyalkylene units (especially polyoxyethylene or polyoxypropylene) or on any polyglyceryl units.

The organopolysiloxane elastomer particles are conveyed in the form of a gel formed from an elastomeric organopolysiloxane included in at least one hydrocarbon-based oil and/or one silicone oil. In these gels, the organopolysiloxane particles are often non-spherical particles.

Non-emulsifying elastomers are especially described in patents EP 242 219, EP 285 886 and EP 765 656 and in patent application JP-A-61-194 009, the content of which is incorporated by way of reference.

Spherical non-emulsifying elastomers that may be used include those sold under the names DC 9040, DC 9041, DC 9509, DC 9505 and DC 9506 by the company Dow Corning.

Organopolysiloxane elastomers with groups MQ, such as those sold by the company Wacker under the names Belsil RG100, Belsil RPG33 and, preferentially, RG80 may also be used in the compositions according to the invention.

The elastomer may also be an emulsifying elastomer.

The term "emulsifying organopolysiloxane elastomer" means an organopolysiloxane elastomer comprising at least one hydrophilic chain, such as polyoxyalkylenated organopolysiloxane elastomers and polyglycerolated silicone elastomers.

The emulsifying organopolysiloxane elastomer may be chosen from polyoxyalkylenated organopolysiloxane elastomers.

The polyoxyalkylenated organopolysiloxane elastomer is a crosslinked organopolysiloxane elastomer that may be obtained by crosslinking addition reaction of diorganopolysiloxane containing at least one hydrogen bonded to silicon and of a polyoxyalkylene containing at least two ethylenically unsaturated groups.

Advantageously, the polyoxyalkylenated organopolysiloxane elastomers may be formed from divinyl compounds, in particular polyoxyalkylenes containing at least two vinyl groups, which react with Si—H bonds of a polysiloxane.

Polyoxyalkylenated elastomers are especially described in U.S. Pat. Nos. 5,236,986, 5,412,004, 5,837,793 and 5,811,487, the content of which is incorporated by reference.

Polyoxyalkylenated organopolysiloxane elastomers that may be used include those sold under the names KSG-21, KSG-20, KSG-30, KSG-31, KSG-32, KSG-33, KSG-210, KSG-310, KSG-320, KSG-330 and KSG-340 by the company Shin-Etsu, and DC9010 and DC9011 by the company Dow Corning.

The emulsifying organopolysiloxane elastomer may also be chosen from polyglycerolated organopolysiloxane elastomers.

The polyglycerolated organopolysiloxane elastomer according to the invention is an organopolysiloxane elastomer that may be obtained by crosslinking addition reaction of diorganopolysiloxane containing at least one hydrogen bonded to silicon and of polyglycerolated compounds containing ethylenically unsaturated groups, especially in the presence of a platinum catalyst.

The polyglycerolated organopolysiloxane elastomer according to the invention is conveyed in gel form in at least one hydrocarbon-based oil and/or one silicone oil. In these gels, the polyglycerolated elastomer is often in the form of non-spherical particles.

Polyglycerolated organopolysiloxane elastomers that may be used include those sold under the names KSG-710, KSG-810, KSG-820, KSG-830 and KSG-840 by the company Shin-Etsu.

Non-emulsifying elastomers that may be used more particularly include those sold under the names KSG-6, KSG-15, KSG-16, KSG-18, KSG-41, KSG-42, KSG-43 and KSG-44 by the company Shin-Etsu, DC9040 and DC9041 by the company Dow Corning, and SFE 839 by the company General Electric.

Emulsifying elastomers that may be used more particularly include those sold under the names KSG-31, KSG-32, KSG-33, KSG-210 and KSG-710 by the company Shin-Etsu.

Advantageously, the organopolysiloxane elastomer under consideration according to the invention is chosen from spherical non-emulsifying organopolysiloxane elastomers, polyglycerolated organopolysiloxane elastomers and polyoxyalkylenated organopolysiloxane elastomers.

It is more particularly a polyoxyalkylenated organopolysiloxane elastomer.

The composition according to the invention may comprise an organopolysiloxane elastomer, alone or as a mixture, in a content ranging from 0.1% to 20% by weight, preferably from 0.2% to 15% by weight and even more preferably from 0.5% to 12% by weight.

A makeup and/or care composition according to the invention may especially be in the form of a suspension, a dispersion, a solution, a gel, an emulsion, especially an oil-in-water emulsion (O/W), water-in-oil emulsion (W/O) or multiple emulsion (W/O/W or polyol/O/W or O/W/O), or in the form of a cream, a mousse, a stick, a dispersion of vesicles, especially of ionic or nonionic lipids, a two-phase or multi-phase lotion, a spray, a powder or a paste.

Advantageously, as stated hereinabove, the compositions according to the invention are anhydrous.

A person skilled in the art may select the appropriate galenical form, and also the method for preparing it, on the basis of his general knowledge, taking into account firstly the nature of the constituents used, especially their solubility in the support, and secondly the intended application of the composition.

In the description and in the examples that follow, unless otherwise mentioned, the percentages are weight percentages.

The examples below are presented as non-limiting illustrations of the field of the invention.

Example 1 of Synthesis of a Supramolecular Polymer:

100 g of dihydroxylated hydrogenated 1,2-polybutadiene polymer (GI3000 from the company Nisso; Mn=4700 measured by GPC according to the protocol described previously) are dried at 80° C., under reduced pressure, overnight. This polymer is dissolved in 400 ml of anhydrous toluene. 25 µl of catalyst (dibutyltin dilaurate) are added and the mixture is heated to 80° C. with stirring, until a uniform solution is obtained. 15 g of isocyanate-functionalized molecule having the following structure:

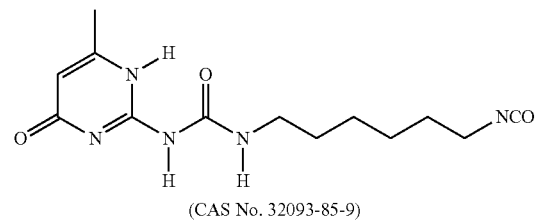

(CAS No. 32093-85-9)

are added as a solution in 300 ml of anhydrous toluene, under a controlled atmosphere at 40° C. The reaction mixture is heated to 100° C. and stirred at this temperature for 4 hours. The reaction is monitored by infrared spectroscopy, with monitoring of the total disappearance of the characteristic peak for isocyanates at 2260 cm$^{-1}$. At the end of the reaction, 100 ml of ethanol are added to remove all trace of residual isocyanate, and the mixture is then filtered, after having added isododecane to make the solution less viscous. The polymer solution is then directly stripped with isododecane.

A solution of the final polymer in isododecane, with a solids content of 21%, is obtained; the polymer is characterized by GPC (Mn=6400 and polydispersity index=1.85) and 1H NMR (spectrum in accordance with what is expected).

Example 2 of Synthesis of a Supramolecular Polymer:

Synthesis of the Ureidopyrimidone Difunctionalized Polymer GI2000

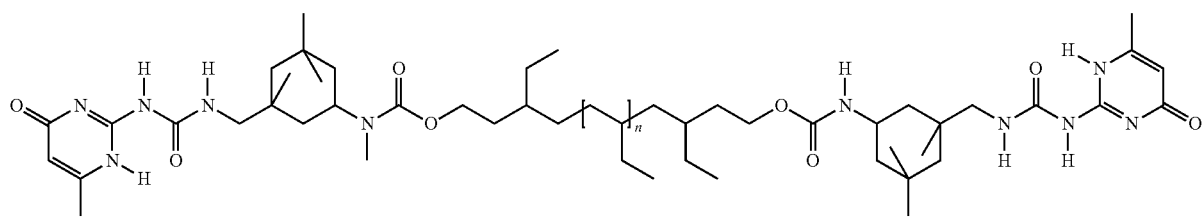

106.1 g of dihydroxylated hydrogenated 1,2-polybutadiene polymer (GI2000 from Nisso, Mn=3300 measured by GPC according to the protocol described previously) are heated in the presence of 22 mg of catalyst (dibutyltin dilaurate) at 80° C. under reduced pressure, for two hours. The temperature of the mixture is reduced to 20° C., under argon, followed by addition of 10 ml of isododecane and 19.3 g of isophorone diisocyanate (IPDI). The mixture is stirred for 16 hours at 20° C. under a controlled atmosphere, and is then heated to 120° C., followed by addition of 25 ml of propylene carbonate. 12 g of 6-methylisocytosine are added, resulting in a homogeneous white suspension. This suspension is heated to 140° C. and stirred at this temperature for 6 hours. The reaction is monitored by infrared spectroscopy, up to the total disappearance of the characteristic peak for isocyanates (2250 cm$^{-1}$). The mixture is then reduced to 30° C., and 400 ml of heptane, 200 ml of THF and 50 ml of ethanol are added, followed by filtration through Celite. The mixture is then stripped with isododecane.

A solution of the polymer in isododecane, with a solids content of 25%, is finally obtained; the polymer is characterized by GPC (Mn=7000 and polydispersity index=2.05).

Example 3 of Synthesis of a Supramolecular Polymer:

99 g of dihydroxylated hydrogenated 1,2-polybutadiene polymer (GI3000 from Nisso, Mn=4700 measured by GPC according to the protocol described previously) are heated in the presence of 22 mg of catalyst (dibutyltin dilaurate) at 80° C., under reduced pressure, for two hours. The temperature of the mixture is reduced to 20° C., under argon, followed by addition of 30 ml of isododecane and 11 g of isophorone diisocyanate (IPDI). The mixture is stirred for 16 hours at 20° C. under a controlled atmosphere, and is then heated to 120° C., followed by addition of 25 ml of propylene carbonate. 8.1 g of 6-methylisocytosine are added, resulting in a homogeneous white suspension. This suspension is heated to 140° C. and stirred at this temperature for 6 hours. The reaction is monitored by infrared spectroscopy, up to the total disappearance of the characteristic peak for isocyanates (2250 cm$^-$). The mixture is then reduced to 30° C., and one litre of heptane is added, followed by filtration through Celite. The mixture is then stripped with isododecane.

A solution of the polymer in isododecane, with a solids content of 20%, is finally obtained; the polymer is characterized by GPC (Mn=4200 and polydispersity index=2.34).

Example 4 of Synthesis of a Supramolecular Polymer:

89 g of dihydroxylated hydrogenated 1,2-polybutadiene polymer (GI3000 from Nisso, Mn=4700 measured by GPC according to the protocol described previously) are heated in the presence of 22 mg of catalyst (dibutyltin dilaurate) at 80° C., under reduced pressure, for two hours. The temperature of the mixture is reduced to 20° C., under argon, followed by addition of 60 ml of isododecane and 11.6 g of 4,4'-dicyclohexylmethane diisocyanate. The mixture is stirred for 16 hours at 20° C. under a controlled atmosphere, and is then heated to 120° C., followed by addition of 40 ml of propylene carbonate. 6.64 g of 6-methylisocytosine are added, resulting in a homogeneous white suspension. This suspension is heated to 140° C. and stirred at this temperature for 8 hours. The reaction is monitored by infrared spectroscopy, up to the total disappearance of the characteristic peak for isocyanates (2250 cm$^{-1}$). The mixture is then cooled to 30° C., and 250 ml of isododecane and 500 ml of heptane are added, followed by filtration through Celite. The mixture is then stripped with isododecane.

A solution of the polymer in isododecane, with a solids content of 22%, is finally obtained; the polymer is characterized by GPC (Mn=10700 and polydispersity index=2.26).

Example 5 of Synthesis of a Supramolecular Polymer:

143.1 g of dihydroxylated hydrogenated 1,2-polybutadiene polymer (GI2000 from Nisso, Mn=3300 measured by GPC according to the protocol described previously) are heated in the presence of 33 mg of catalyst (dibutyltin dilaurate) at 80° C., under reduced pressure, for two hours. The temperature of the mixture is reduced to 20° C., under argon, followed by addition of 85 ml of isododecane and 30.8 g of 4,4'-dicyclohexylmethane diisocyanate. The mixture is stirred for 16 hours at 20° C. under a controlled atmosphere, and is then heated to 120° C., followed by addition of 70 ml of propylene carbonate. 22.6 g of 6-methylisocytosine are added, resulting in a homogeneous white suspension. This suspension is heated to 140° C. and stirred at this temperature for 8 hours. The reaction is monitored by infrared spectroscopy, up to the total disappearance of the characteristic peak for isocyanates (2250 cm$^-$). The mixture is then cooled to 20° C., and 700 ml of isododecane and 500 ml of heptane are added, followed by filtration through Celite. The mixture is then stripped with isododecane.

A solution of the polymer in isododecane, with a solids content of 20%, is finally obtained; the polymer is characterized by GPC (Mn=8400 and polydispersity index=2.00).

Example 6: Effect of a Filler According to the Invention on the Tacky Nature of Cosmetic Formulae of Fluid Foundation Type Five makeup formulae according to the invention having the following composition and four comparative formulae were prepared (the percentages indicated are weight percentages).

Table 1 below gives the formulation of five compositions according to the invention and of four control compositions.

TABLE 1

|   |   | Formula 1 (weight %) In accordance with the invention | Formula 2 (weight %) In accordance with the invention | Formula 3 (weight %) In accordance with the invention | Formula 4 (weight %) In accordance with the invention | Formula 5 (weight %) In accordance with the invention |
|---|---|---|---|---|---|---|
| A1 | Solution of ureidopyrimidone difunctionalized supramolecular polymer GI2000 at 25% in isododecane, as prepared in Example 2 | 56 (i.e. 14% solids) | 56 (i.e. 14% solids) | 56 (i.e. 14% solids) | 56 (i.e. 14% solids) | 56 (i.e. 14% solids) |
|   | Isododecane | 26.5 | 26.5 | 26.5 | 26.5 | 26.5 |
| A2 | Isododecane | 2.5 | 2.5 | 2.5 | 2.5 | 2.5 |
|   | Pigments | 10 | 10 | 10 | 10 | 10 |
| B | Silica microspheres (Silica Beads SB 700) |   |   |   |   |   |
|   | Amorphous silica microspheres (particle size: 3 microns) (Miyoshi Kasei, Sunsphere H-33, AGC Si-TECH) | 5 |   |   |   |   |
|   | Silica Silylate (Aerogel beads VM-2270, Dow Corning) |   | 5 |   |   |   |

TABLE 1-continued

| | | | | | |
|---|---|---|---|---|---|
| Ethylene glycol dimethacrylate/lauryl methacrylate copolymer (Polytrap 6603 Adsorber, Amcol) | | | 5 | | |
| Amorphous hollow silica particles (Silica Shells, Kobo) | | | | 5 | |
| Polymethyl methacrylate/ethylene glycol dimethacrylate powders (Microsponge 5640, Cardinal Health Technologies) | | | | | 5 |

| | | Formula 6 (weight %) Comparative (without filler in accordance with the invention) | Formula 7 (weight %) Comparative (with a filler not in accordance with the invention) | Formula 8 (weight %) Comparative (with a filler not in accordance with the invention) | Formula 9 (weight %) Comparative (with a filler not in accordance with the invention) |
|---|---|---|---|---|---|
| A1 | Solution of ureidopyrimidone difunctionalized supramolecular polymer GI2000 at 25% in isododecane, as prepared in Example 2 | 56 (i.e. 14% solids) | 56 (i.e. 14% solids) | 56 (i.e. 14% solids) | 56 (i.e. 14% solids) |
| | Isododecane | 31.5 | 26.5 | 26.5 | 26.5 |
| A2 | Isododecane | 2.5 | 2.5 | 2.5 | 2.5 |
| | Pigments | 10 | 10 | 10 | 10 |
| B | Silica microspheres (Silica Beads SB 700) | | 5 | | |
| | Nylon 12 (Orgasol 2002 from the company Arkema) | | | 5 | |
| | Starch (Dry Flo Plus from Akzo Nobel) | | | | 5 |

Procedure:

The constituents of phase A2 were weighed out. The mixture was ground in a three-roll mill.

Next, the constituents of phase A1 were weighed out in the main beaker and placed in a Rayneri blender. Phase A2 was then added. After stirring for a few minutes, phase B was incorporated.

Evaluation of the Formulae:

The tacky aspect of the formulae 1 to 9 thus obtained was evaluated according to the protocol defined below.

Protocol for Evaluating the Tack:

Each formula was applied by finger to the forearm. The amount applied was 0.05 g.

The tacky nature of the deposit was evaluated by finger, during drying, one minute after application, at 25° C. To do this, a finger was applied, after the specified interval, onto the deposit and the tack was assessed by the person on removal of his finger from the deposit.

For the measurements performed, it is considered that:
+ No tack during drying
++ Slight tack effect during drying
+++ Moderate tack effect during drying
++++ Strong tack effect during drying As regards the oil absorption measurements, they were performed by measuring the wet point according to the method described previously.

The following results were obtained:

TABLE 2

| Compositions | Formula 1 (Sunsphere H-33 ®) | Formula 2 (Aerogel ®) | Formula 3 (Polytrap ® 6603) | Formula 4 (Silica Shells ®) | Formula 5 (Microsponge 5640) |
|---|---|---|---|---|---|
| Oil absorption (ml/g) | 3.70 | 10.90 | 6.56 | 5.50 | 1.55 |
| Tack evalution | + | + | ++ | ++ | ++ |

| Compositions Controls | Formula 6 (no filler) | Formula 7 (Silica Beads) | Formula 8 (Orgasol 200) | Formula 9 (Dry Flo Plus) |
|---|---|---|---|---|
| Oil absorption (ml/g) | — | 1.33 | 1.1 | 0.4 |
| Tack evaluation | ++++ | ++++ | ++++ | ++++ |

It emerges from these results that the deposits of the compositions in accordance with the invention show significantly reduced tacky nature relative to the control compositions 6 to 9. The compositions according to the invention are consequently more comfortable on application and immediately after.

Example 7: Cosmetic Formula of Fluid Inverse Emulsion (Water-in-Oil) Foundation Type The following composition was prepared

TABLE 3

| | Ingredients | % |
| --- | --- | --- |
| A1 | Solution of ureidopyrimidone difunctionalized supramolecular polymer GI2000 at 25% in isododecane, as prepared in Example 2 | 40 (i.e. 10% by weight of polymer solids) |
| | Isododecane | 10 |
| A2 | PEG-30 dipolyhydroxystearate (Cithrol DPHS-SO-(MV), Croda) | 2.5 |
| A3 | Isododecane | 2.5 |
| | Pigments | 10 |
| B | Amorphous silica microspheres (particle size: 3 microns) (Miyoshi Kasei, Sunsphere H-33, AGC Si-TECH) | 5 |
| C | Water | 29.5 |
| | Preserving agents | 0.5 |

Procedure:

The constituents of phase A1 are weighed out in a beaker, with stirring using a Moritz blender, while maintaining the ambient temperature at 50° C. The premolten phase A2 is then added, with continued stirring.

Phase A3 is prepared separately by milling the pigments in a three-roll mill, and this phase is then added with stirring to the preceding mixture.

To prepare phase B, the water is brought to the boiling point and the other constituents of phase B are then added. The temperature of phase B is cooled to about 50° C.

The emulsion is prepared at 50° C. The two phases must have a temperature in the region of 50° C. The aqueous phase B is poured slowly into phase A while gradually increasing the stirring speed of the Moritz blender up to 2500 rpm. After addition, the mixture is stirred for a further 10 minutes at room temperature. Phase C is then added and the mixture is stirred for 5 minutes.

Example 8: Cosmetic Formula of Fluid Direct Emulsion (Oil-in-Water) Foundation Type The following composition was prepared

TABLE 4

| | Ingredients | % |
| --- | --- | --- |
| A1 | Water | 44.1 |
| | Preserving agents | 0.5 |
| A2 | Sodium lauroyl sarcosinate as an aqueous 30% solution (Oramix L30, SEPPIC) | 1.8 |
| A3 | Pigments | 10 |
| | Water | 6.7 |
| B1 | Solution of ureidopyrimidone difunctionalized supramolecular polymer GI2000 at 25% in isododecane, as prepared in Example 2 | 20 (i.e. 5% polymer solids) |
| | Isododecane | 4 |
| B2 | Stearic acid | 2 |
| | Glyceryl mono/distearate | 2.9 |
| | Stearyl alcohol | 1 |
| | Glyceryl isostearate | 2 |

TABLE 4-continued

| | Ingredients | % |
| --- | --- | --- |
| C | Amorphous silica microspheres (particle size: 3 microns) (Miyoshi Kasei, Sunsphere H-33, AGC Si-TECH) | 5 |

Procedure:

To prepare phase A1, the water is brought to the boiling point and the other constituents of phase A1 are then added. The mixture is stirred using a Moritz blender. The temperature of phase A1 is lowered to about 50° C. and phase A2 is then introduced.

Phase A3 is prepared separately by milling the pigments in a three-roll mill, and this phase is then added with stirring to the preceding mixture.

The constituents of phase B2 are melted on a water bath. When the mixture has cooled to 45° C., they are added to phase B1 that is also heated to 45° C. The whole is stirred with a Rayneri blender for 10 minutes.

The emulsion is prepared at 45° C. The two phases must have a temperature in the region of 45° C. The aqueous phase B is poured slowly into phase A while gradually increasing the stirring speed of the Moritz blender up to 2500 rpm. After addition, the mixture is stirred for a further 10 minutes at room temperature. Phase C is then added and the mixture is stirred for 5 minutes.

Example: 9 Cosmetic Lip Formula

A lip composition is prepared, comprising (weight %):

TABLE 5

| Ingredients | (weight %) |
| --- | --- |
| Solution of ureidopyrimidone difunctionalized supramolecular polymer GI2000 at 25% in isododecane, as prepared in Example 2 | 80 (i.e. 20 weight % of solids) |
| Phenyl silicone 15 cSt (Diphenylsiloxyphenyl trimethicone) (KF 56 A, Shin-Etsu) | 14 |
| Amorphous silica microspheres (particle size: 3 microns) (Miyoshi Kasei, Sunsphere H-33, AGC Si-TECH) | 5 |
| Pigments | 1 |

The invention claimed is:

1. A composition for making up and/or caring for skin and/or lips, comprising, in a physiologically acceptable medium:

at least one supramolecular polymer represented by the following formula:

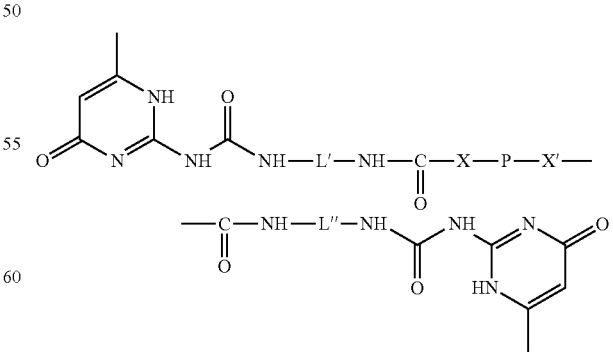

where:
L' and L" are both isophorone groups;
X, X'=O; and

P is hydrogenated 1,2-polybutadiene; and
at least one filler with an oil uptake, measured according to standard NF T 30-022 of greater than or equal to 1.5 ml/g.

2. The composition according to claim 1, comprising from 0.1% to 60% by weight of supramolecular polymer solids relative to a total weight of the composition.

3. The composition according to claim 1, wherein the filler has an oil uptake ranging from 1.5 ml/g to 20 ml/g.

4. The composition according to claim 1, comprising from 0.5% to 40% by weight of filler(s) with an oil uptake of greater than or equal to 1.5 ml/g relative to a total weight of the composition.

5. The composition according to claim 1, wherein the filler(s) with an oil uptake of greater than or equal to 1.5 ml/g and the supramolecular polymer are present in a polymer(s)/filler(s) with an oil uptake of greater than 1.5 ml/g in a weight ratio of greater than 1.

6. The composition according to claim 1, wherein the filler with an oil uptake of greater than or equal to 1.5 ml/g is a mineral or organic powder.

7. The composition according to claim 1, wherein the filler with an oil uptake of greater than 1.5 ml/g is a silica powder.

8. The composition according to claim 1, wherein the composition is anhydrous.

9. The composition according to claim 1, further comprising at least one fatty phase.

10. A cosmetic process for making up and/or caring for skin and/or lips, including at least application to the skin and/or the lips of a composition comprising, in a physiologically acceptable medium:

at least one supramolecular polymer represented by the following formula:

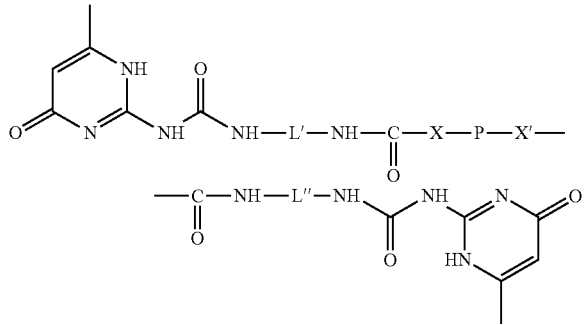

where;
L' and L" are both isophorone groups;
X, X'=O; and
P is hydrogenated 1,2-polybutadiene; and
at least one filler with an oil uptake, measured according to standard NF T 30-022 of greater than or equal to 1.5 ml/g.

11. The composition according to claim 1, wherein the filler with an oil uptake of greater than or equal to 1.5 ml/g is selected from the group consisting of silicas, silica silylates, polyamide powders, powders of acrylic polymers, perlites, and magnesium carbonate.

* * * * *